United States Patent
Yoon

Patent Number: 6,159,207
Date of Patent: Dec. 12, 2000

[54] PROTECTED ABLATION METHOD AND APPARATUS

[76] Inventor: InBae Yoon, 2101 Highland Ridge Dr., Phoenix, Md. 21131

[21] Appl. No.: 09/124,008

[22] Filed: Jul. 29, 1998

Related U.S. Application Data

[60] Provisional application No. 60/054,391, Jul. 31, 1997.

[51] Int. Cl.⁷ .................................................. A61B 18/18
[52] U.S. Cl. ............................................................. 606/41
[58] Field of Search .............................. 606/41, 46, 119, 606/135, 148, 205; 607/96, 98, 99, 100, 101, 102

[56] References Cited

U.S. PATENT DOCUMENTS

| | | | |
|---|---|---|---|
| 5,876,401 | 3/1999 | Schulze et al. | 606/51 |
| 5,925,038 | 7/1999 | Panescu et al. | |
| 5,938,658 | 8/1999 | Tu | 606/41 |
| 6,036,688 | 3/2000 | Edwards | 606/34 |

*Primary Examiner*—Linda C. M. Dvorak
*Assistant Examiner*—R. Kearney
*Attorney, Agent, or Firm*—Blank, Rome, Comisky & McCauley LLP

[57] ABSTRACT

A method and apparatus for protected ablation of anatomical tissue. A protective cap is disposed around tissue within an anatomical cavity by an endoscopic device or through open surgery techniques. The tissue can then be subject to ablation at high energy for a relatively long period of time, if necessary to ablate the tissue, without damaging surrounding organs or other tissue. The protective cap can be inserted endoscopically in a closed position in which it is compact radially and can be opened after being inserted into the body cavity to be placed around the tissue. The protective cap can be a thermal insulator, an electrical insulator, merely a physical pad to protect surrounding tissue, or of any desired characteristic for protection.

30 Claims, 18 Drawing Sheets

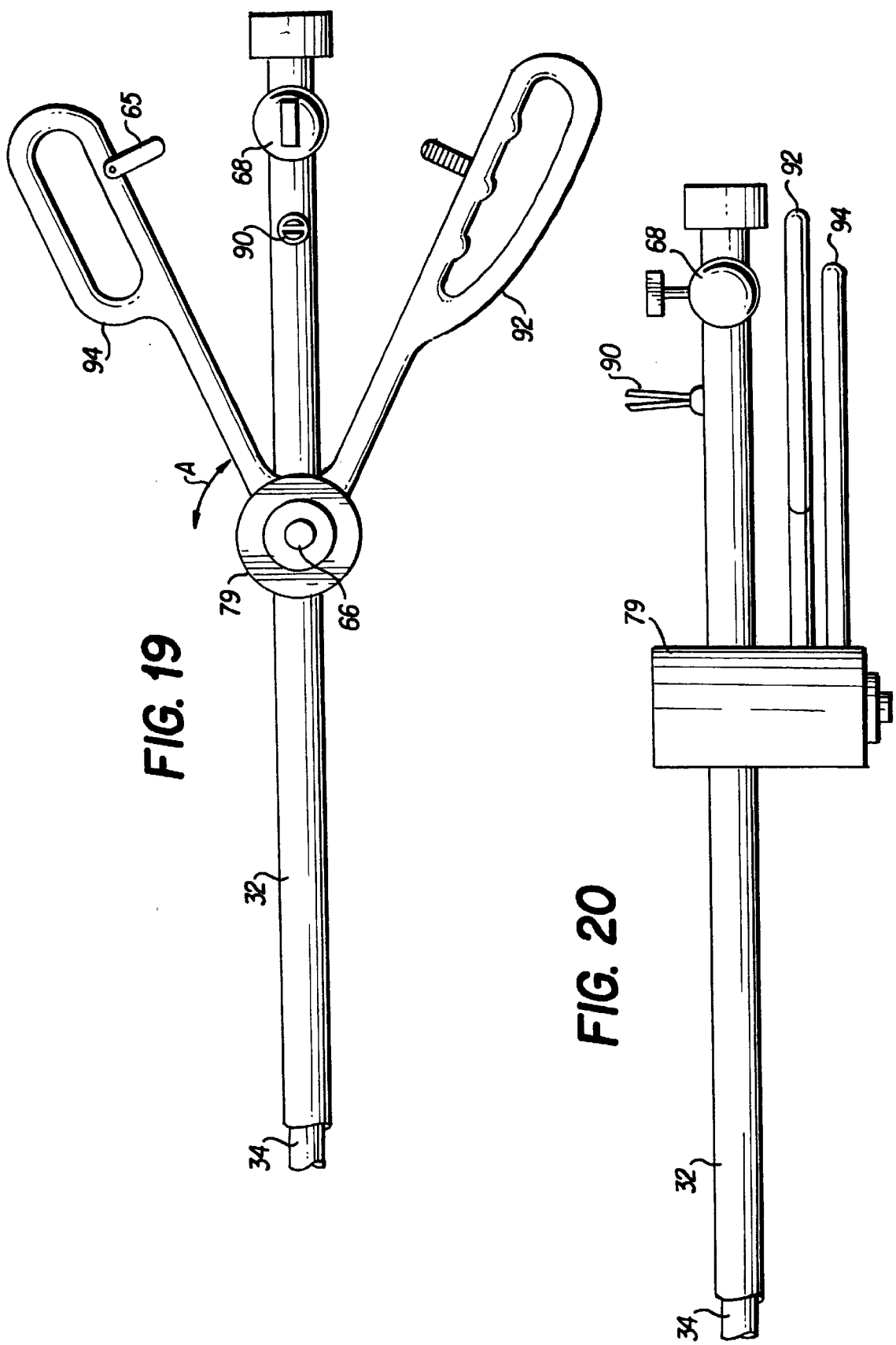

PROTECTED ABLATION METHOD AND APPARATUS

This application claims benefit to provisional application Ser. No. 054,391, filed Jul. 31, 1997.

BACKGROUND OF THE INVENTION

1. Field of the Invention

The subject invention relates to a method and apparatus for ablating anatomical organs, lumens or other tissue and more particularly to a protective cover that isolates the tissue to be ablated from surrounding tissue to permit complete and rapid ablation, or other manipulation, of the tissue without damaging surrounding tissue.

2. Description of the Related Art

Anatomical organs, such as the uterus, gall bladder, large intestine, and the like, can develop abnormal conditions, such as excessive bleeding. It is known to treat such abnormal organ conditions by removal of a portion or an entirety of the organ. However, removal of an organ ordinarily requires invasive surgery and general anesthesia and thus is expensive and presents a relatively high risk to the patient. Also, removal of an organ eliminates the function of the organ entirely. This may require additional treatment to replace the organ function. Further, removal of an organ can be psychologically traumatic to the patient, particularly in the case of reproductive organs.

It is also known to ablate tissue by heating the tissue (thermal ablation), freezing the tissue (cryogenic ablation), mechanically cutting or scraping the tissue, or otherwise applying energy or manipulation of the tissue. The terms "ablating" and "ablation" as used herein broadly refer to killing, removing, or otherwise destroying or altering tissue or the function of tissue, such as through cauterization, coagulation, sclerosing, necrosing, removal or the like. Ablation is accomplished by introducing an ablating member to an area proximate the damaged tissue. Thermal ablating members can include a laser, an RF electrode, a radiation member, an electrically resistive coil, a scraping device, or any other method of delivering energy. Lasers are inherently focused to a small area and thus laser ablation requires that the surgeon direct the laser at the particular tissue to be ablated and, if the area to be ablated is large, the surgeon must move the laser to cover the entire area as if painting the area. Also, if the laser energy is too high, or the surgeon lingers too long on one area, the laser energy can cause the tissue to be cut, perforated, or overheated and other organs can be damaged. Similarly, other thermal and cryogenic devices must be carefully applied and controlled to insure that the abnormal tissue is affected without damaging other normal tissue or organs that are proximate the damaged tissue. Therefore, known ablation techniques use endoscopes or the like to inspect the condition of the tissue and complex controls to control the application of energy to the damaged tissue.

For example, a diseased condition of the uterus, known as endometriosis, is often treated by ablating the diseased tissue, i.e. the inner layer of the uterus known as the endometrium. Of course, it is desirable to cause necrosis in the endometrium without damaging other surrounding organs. Since other organs, such as the bladder, are closely pressed against the uterus, it is quite difficult to avoid damage to other organs. Thus, conventionally, the endometrium had to be ablated, by applying heat for example, without heating the outer layer of the uterus known as the myometrium. Therefore, known ablating techniques for treating the uterus have applied energy in relatively low levels for a precisely controlled period of time. For example, the tissue is heated to about 200° F. (in the case of thermal ablation) or cooled to below 32° F. (in the case of cryogenic ablation) for several minutes. This often fails to induce necrosis in the entire endometrial layer because the inner surface of the uterus is not smooth and has many crevices, for example areas proximate the fallopian tubes, to which it is difficult to apply energy and the thickness of the endometrium often varies. Also, higher levels of heating or cooling can damage surrounding organs if applied for too long and thus precise time and temperature control is required. Also, a procedure known as "dilation and curretage" (D and C) is often used to treat endometriosis or other uteran abnormalities. The, D and C procedure requires mechanical scraping. If the scraping is not carefully controlled, the myometrium can be damaged and even perforated, in which case surrounding organs can be damaged. Also, it is difficult to ensure that all of the diseased tissue is removed.

U.S. Pat. No. 3,645,265 discloses a spring member that is inserted into the uterus and then expanded to press against the uterine wall. The spring is then used as a cautery electrode to cause necrosis. However, heating is intensified at portions of the uterine wall that contact the spring and thus localized higher degrees of ablating may occur. In order to cause necrosis in large areas of the uterus, such as in the entire endometrium, it may be necessary to apply excessive heat to areas which contact the spring. This can damage surrounding tissue.

U.S. Pat. No. 5,105,808 discloses an applicator having a distendable bladder that is inserted into the uterus. A heated fluid is introduced into the bladder to cause necrosis of the uterus. However, the bladder may not contact all of the crevices of the uterine wall and thus incomplete necrosis or undesired tissue damage may occur. U.S. Pat. No. 5,449,380 attempts to solve this problem by providing spring members in an inflatable bladder that cause the bladder to conform more closely to a standard shape of a uterus. However, since each uterus is shaped differently, even the device disclosed in U.S. Pat. No. 5,449,380 may fail to reliably contact all portions of the endometrium and thus may exhibit the limitations noted above.

U.S. Pat. No. 5,242,390 discloses the introduction of heated liquid onto the uterus for ablation. U.S. Pat. No. 5,242,390 also discloses that silicone polymer rings or physiologic saline solution can be disposed internally in the uterus to protect the fallopian tubes from damage due to the applied heat. However, these patents also fail to disclose any protection for other surrounding organs.

U.S. Pat. No. 5,575,788 discloses an ablating apparatus having an expandable porous member. Electrolytic solution is released through the porous member and an electrically conductive conforming member acts as an ablating electrode. The porosity of the porous member varies to concentrate the electrolytic solution at desired areas. U.S. Pat. Nos. 5,277,201, 5,443,470, and 5,433,708 disclose limiting temperature to prevent damage to normal tissue. However, no adequate solution exists for preventing damage to surrounding organs while completely ablating a damaged organ. Accordingly, conventional uterine ablating techniques are not reliable and must be repeated several times in many patients to be effective. Therefore, most uterine problems are addressed by removing the uterus. This can cause physical and psychological trauma. Often this trauma can inhibit the body's immune system and ability to generate anticancer agents or the like.

Uterine ablating is ordinarily accomplished by a device that is inserted vaginally. However, it is well known to accomplish ablation of other organs using endoscopic or other minimally invasive devices that are inserted through a portal sleeve disposed in an aperture formed in the patient's skin by an obturator, such as a trocar.

Finally, the potential for error in known procedures makes it necessary for the procedures to be carried out by a physician in a surgical environment. This increases the cost of the procedures.

SUMMARY OF THE INVENTION

The invention is directed to solving the problems in the prior art noted above.

It is an object of the invention to ablate in the uterus, or any organ or tissue, in part or in its entirety without damaging surrounding organs.

It is another object of the invention to permit the uterus, or any other organ or tissue, to be heated to a relatively high temperature to completely necrose the organ or tissue.

It is another object of the invention to detect the temperature of tissue during an ablating process to permit proper control of an ablating process.

It is still a further object of the invention to place a protective cover around an organ to prevent damage to surrounding organs when the organ is heated to a relatively high temperature, cooled to a relatively low temperature, or otherwise manipulated.

Finally, it is an object of the invention to reduce the level of skill required for ablating procedures and thus reducing the risk and cost of ablating procedures.

It is still further an object of the invention to avoid physical and psychological trauma associated with the physical removal of anatomical organs and thus to facilitate the generation of natural anticancer agents or other desirable agents by the patient's body.

To achieve these objects, the invention includes a protective cap made of protective members that can be placed around an organ or other tissue to surround or cover the organ or tissue. After being covered by the protective cap, the organ or tissue can then be heated, frozen, scraped, or otherwise manipulated, without damaging surrounding organs. The protective members can be of various shapes and sizes and can be expandable between open and closed positions to permit insertion endoscopically, culdescopically, culpescopically, or in another manner. Temperature sensors can be provided in the protective cap to monitor and control the ablating process to ensure that healthy tissue is not damaged. Further, a heating element, or other type of energy source, can be disposed in or on the protective cap to ablate tissue covered by the protective cap. The protective cap can be a thermal insulator to protect surrounding tissue from ablating heat, a mechanical cover to prevent instruments from piercing surrounding tissue, a radiation barrier to protect surrounding tissue from ablating radiation, or another type of protector.

BRIEF DESCRIPTION OF THE DRAWINGS

FIG. 19 is a side view of an alternative handle arrangement;

FIG. 20 is a top view of the alternative handle arrangement; and

DETAILED DESCRIPTION OF THE PREFERRED EMBODIMENTS

Figure 1:
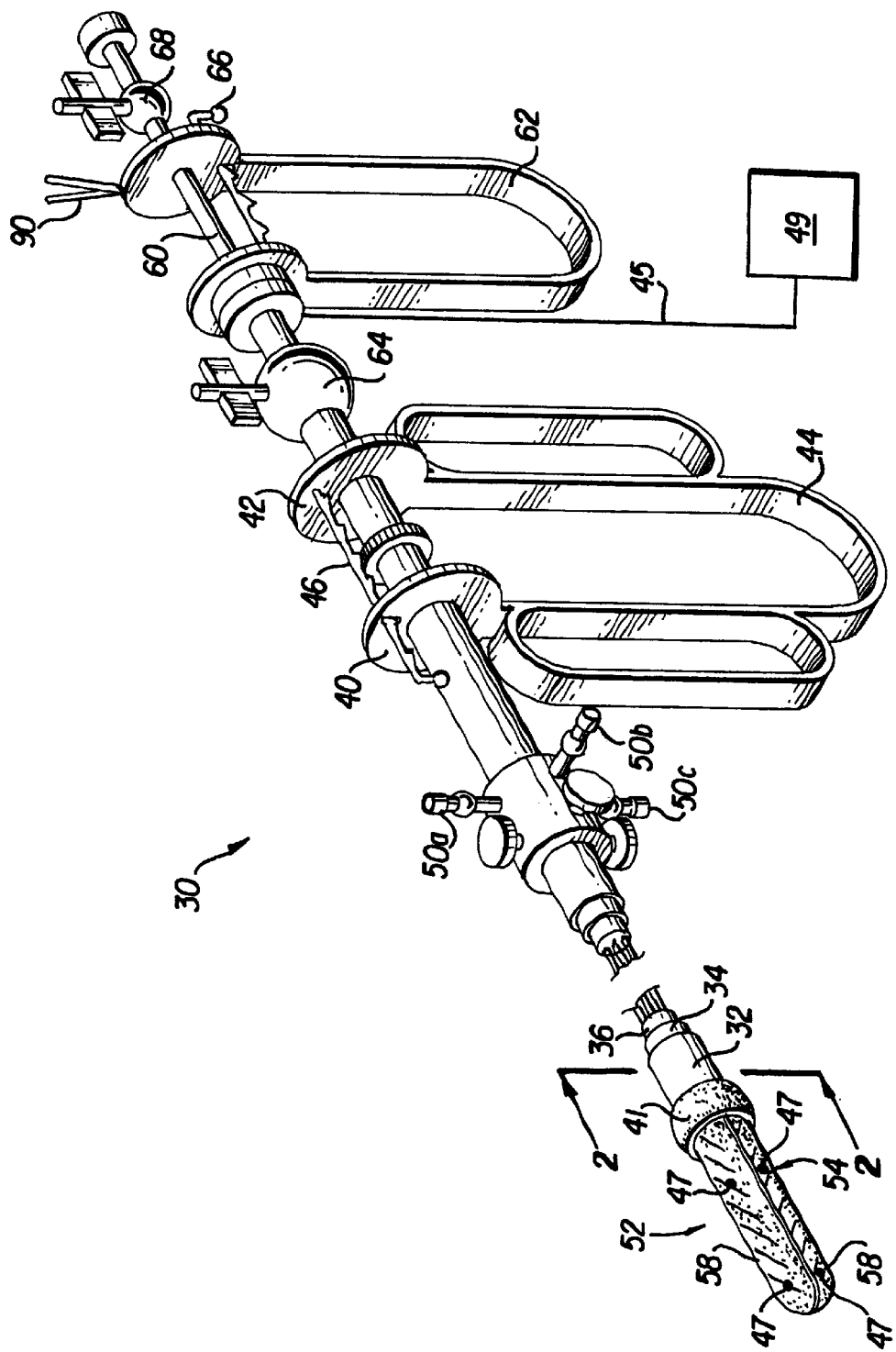
FIG. 1 is a perspective view of the first preferred embodiment with the protective members in a closed position.

Protection device 30 of the first preferred embodiment is illustrated in FIG. 1 and includes tubular outer member 32, tubular inner member 34, and insulating tube 36, all being disposed essentially concentrically with respect to one another. Outer member 32 is slidable over inner member 34 and terminates proximally at flange 40. Inner member 34 terminates proximally at flange 42. Handle 44, is essentially U-shaped, is connected to flange 40 at one end and is connected to flange 42 at the other end. Handle 44 is resiliently biased to the position illustrated in FIG. 1 and is adapted to be held by a surgeon and, when compressed by the surgeon, causes outer member 32 to slide proximally with respect to inner member 34, as shown in FIG. 4.

Lock device 46 is rotatably mounted in a hole formed through flange 42 and passes through a hole formed in flange 40. Serrated teeth are formed on one side of lock device 46. When lock device 46 is rotated to place the teeth in the upward position, the teeth engage with flange 40 to lock flange 40 in place relative to flange 42. When the teeth face downward, as in FIG. 1, flange 40 and flange 42 can be moved freely with respect to one another against the biasing force of handle 44. The teeth can be sloped on one side to provide a one way ratcheting effect.

Figure 2:
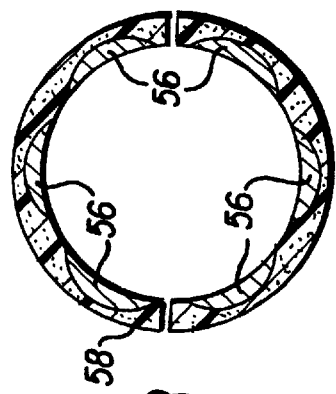
FIG. 2 is a cross-sectional view taken along line 2—2 in FIG. 1.

As best illustrated in FIG. 2, insulating tube 36 is formed of a length of very thin tubular material and is disposed at least partly inside inner member 34 to define a lumen in which operating channels 38a–38c are formed. Also, insulating tube 36 can be made of an electrically or thermally insulating material to permit an electrical device or a thermal device such as cautery electrodes to be insulated from the rest of the instrument. Insulating tube 36 can be omitted if such insulation is not required. Of course, there can be more or less than the three operating channels 38a–38c as needed. Optical fibers 37 can be disposed in insulating tube 36 to permit light to be directed into an anatomical cavity when the distal end of protection device 30 is disposed in the cavity. A known optical coupling device can be provided to couple optical fibers 37 to a proximal end light source. Also, central lumen 39 is defined through a center of protection device 30 for passage of a known type of endoscope or other instrument, as will be described in greater detail below. Operating channels 38a–38c and central lumen 39 can be defined by thin walled tubular members or merely by void spaces defined between optical fibers 37. As shown in FIG. 1, port and valve combinations 50a–50c are provided and communicate respectively with operating channels 38a–38c through slots formed in outer member 32, inner member 34, and insulating tube 36. Port and valve combinations 50a–50c permit operating channels 38a–38c to be selectively coupled to fluid sources, vacuum sources, or other devices to permit operating channels 38a–38c to be used for irrigation, suction, dispensing medicaments, aspiration, or the like.

Surgical instrument 60 (only a proximal end of which can be seen in FIGS. 1 and 4), having any appropriate end effector such as a needle, cutting blade, cautery electrode, clip applicator or the like, can be inserted in central lumen 39 and the end effector can be advanced out of a distal end of protection device 30 when needed by compressing handle 62 which is coupled to inner member 34 and a proximal end of instrument 60. When instrument 60 is removed from central lumen 39, valve assembly 64 can be closed to seal central lumen 39 to avoid loss of fluids or pneumoperitoneum from the anatomical cavity. Lock device 63, similar to lock device 46, can be provided on handle 62 to fix instrument 60 in a desired position. Also, a channel can be defined in surgical instrument 60 and port and valve combination 68 provides access to this channel to permit an endoscope, or other viewing device, or the like to be inserted through surgical instrument 60 or to permit suction or fluid injection through instrument 60.

Figure 3B:
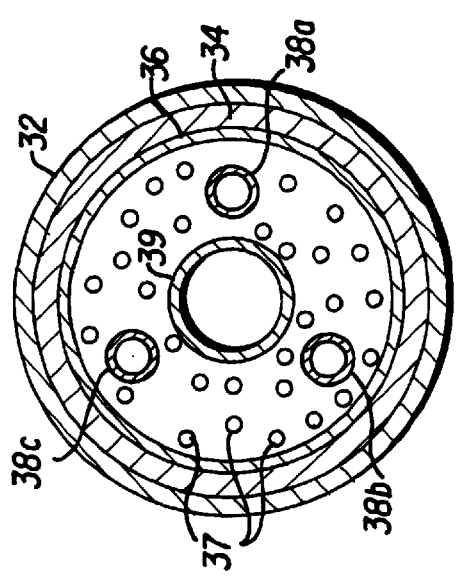
FIG. 3B is a cross-sectional view of the flexible extending arms of FIG. 3A taken along line 3—3.
Figure 3A:
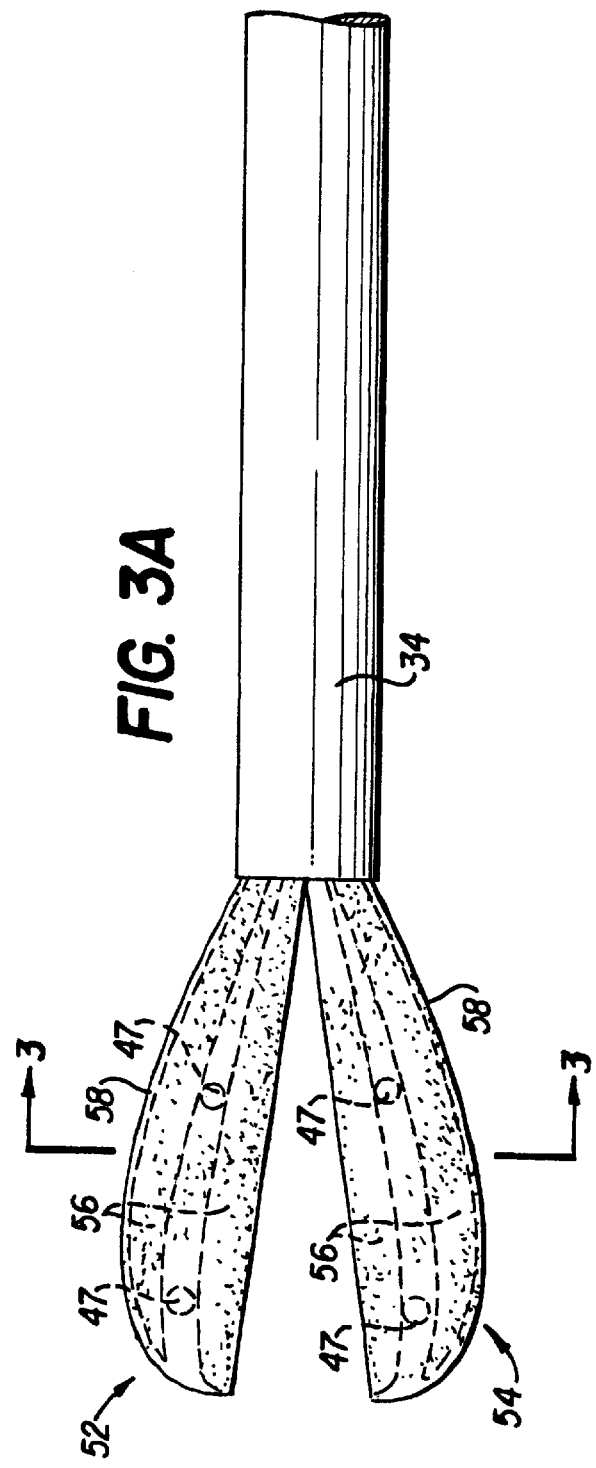
FIG. 3A illustrates a distal end of the inner member of the first preferred embodiment.

Protective members 52 and 54 in a form of cupping elements extend from a distal end of inner member 34 and are formed of protective covers 58 stretched over spoon-like flexible extending arms 56, as best illustrated in FIGS. 3A and 3B showing a distal end of inner member 34 and protective members 52 and 54 removed from outer member 32 for illustrative purposes. FIG. 1 shows the closed position of protective members 52 and 54 wherein outer member 32 is slid distally over flexible extending arms 56 to an extent that presses flexible extending arms towards a longitudinal central axis of insulation application device. In the closed position, insulating members 52 and 54 assume a substantially cylindrical shape and are contained substantially within the radial dimensions of outer member 32. The closed position facilitates insertion into an anatomical cavity through a portal sleeve, other small opening, or the like. When handle 44 is compressed by the surgeon, flange 40 and outer member 32 move in a proximal direction to permit flexible extending arms 56 to move outward to assume the position illustrated in FIGS. 3A and 4 wherein protective members 52 and 54 each assume a spoon-like shape with a gap defined between protective members 52 and 54. The size of the gap can be varied by moving outer member 32 in the proximal and distal directions. Flexible extending arms 56 in this embodiment are relatively wide plates for increased rigidity. However, thinner or fewer arms can be used to provide better viewing through an endoscope or the like disposed in channel 39 or instrument 60.

Flexible extending arms 56 can be made of any resilient or shape memory material that assumes the desired shape or can be made of a plurality of rigid members pivotally linked together and biased to the desired position by a biasing member such as a spring. Protective covers 58 can be made of any flexible material that is biocompatible, such as known biocompatible sponge materials or the like. Also sponge 41 can be disposed around a distal end of outer member 32 to be used as a blunt dissecting tool to separate tissue in the manner described below before inserting insulating members 52 or 54 between the tissue. FIG. 1 shows sponge 41 dry and FIG. 4 shows sponge 41 enlarged after absorbing fluid.

Operation of protection device 30 in combination with an ablating device is described below. The operation of the preferred embodiment is described with reference to gall bladder ablation and uterine ablation in a female patient. However, the invention can be used for ablating any organ or other tissue, such as ovaries, the liver, or the prostate gland or for performing other procedures. With protective members 52 and 54 in the closed position illustrated in FIG. 1, a distal end of protection device 30 is inserted into the patient's abdomen, through a portal sleeve or the like, proximate the fundus of the uterus. Protection device 30 is then manipulated while viewing the operation through an endoscope inserted through a separate puncture site or through an endoscope inserted through one of central lumen 29, operating channels 38a–c or instrument 60. Handle 44 can be compressed immediately after insertion of the distal end by the surgeon to open insulating members 52 and 54 at least partially to permit viewing in the case of an endoscope inserted through protection device 30.

Figure 4A:
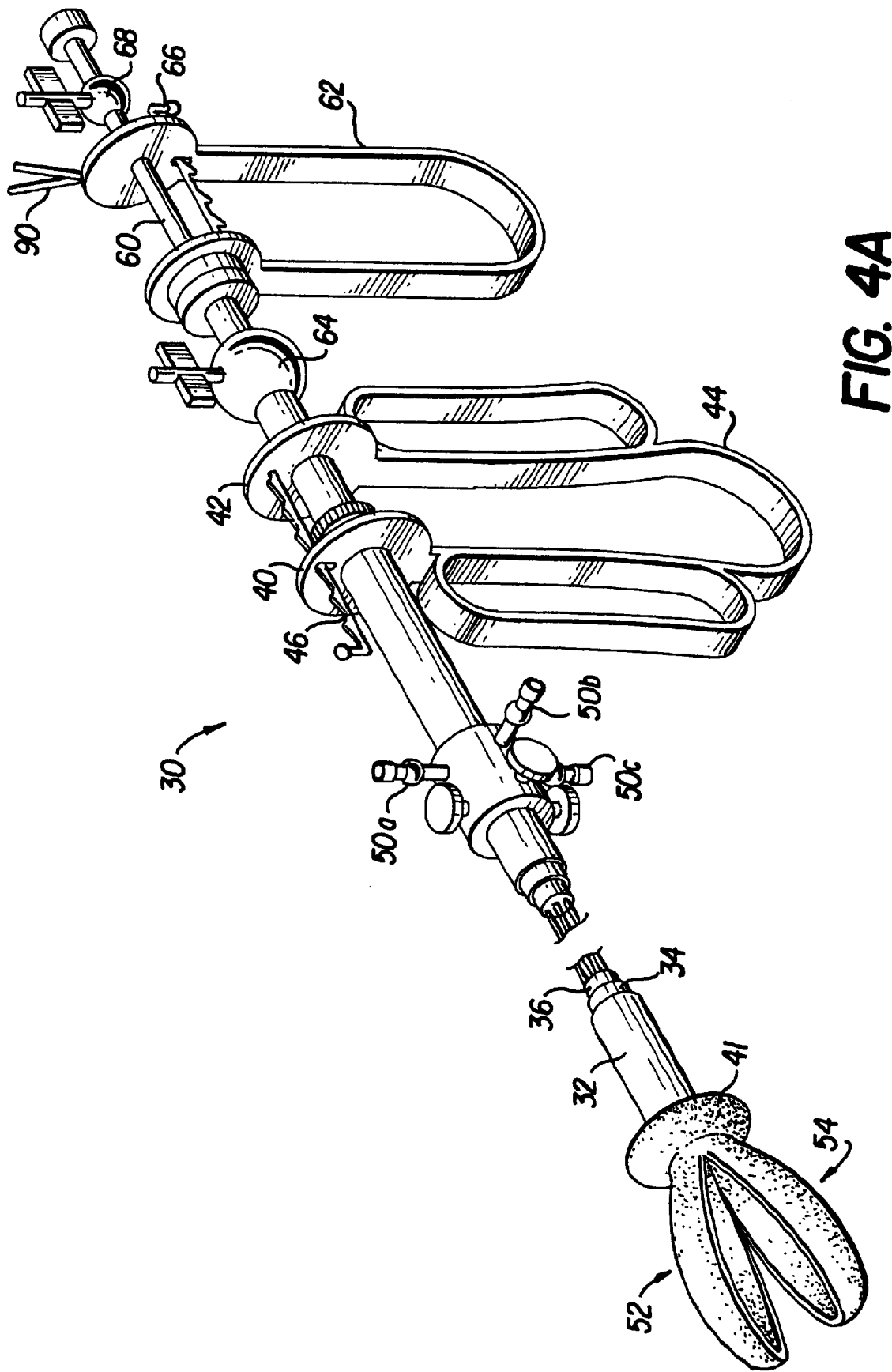
FIG. 4A is a perspective view of the first preferred embodiment with the protective members in an open position.
Figure 4B:
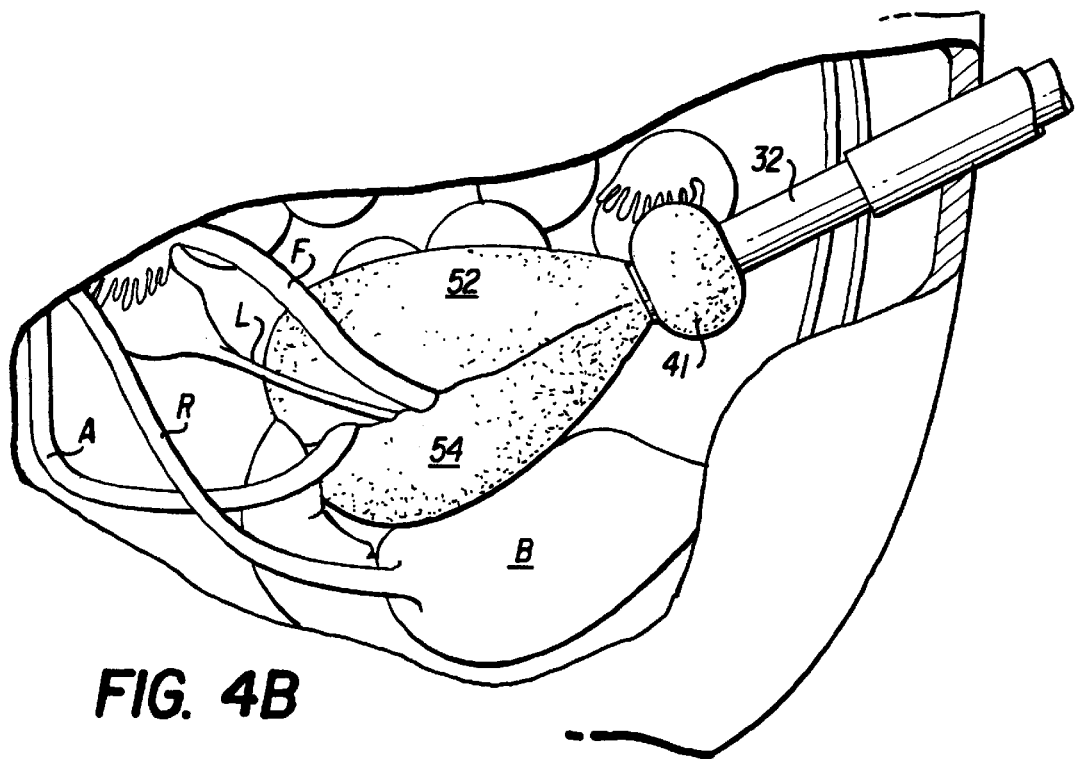
FIG. 4B is a die view of the first preferred embodiment in use.
Figure 4C:
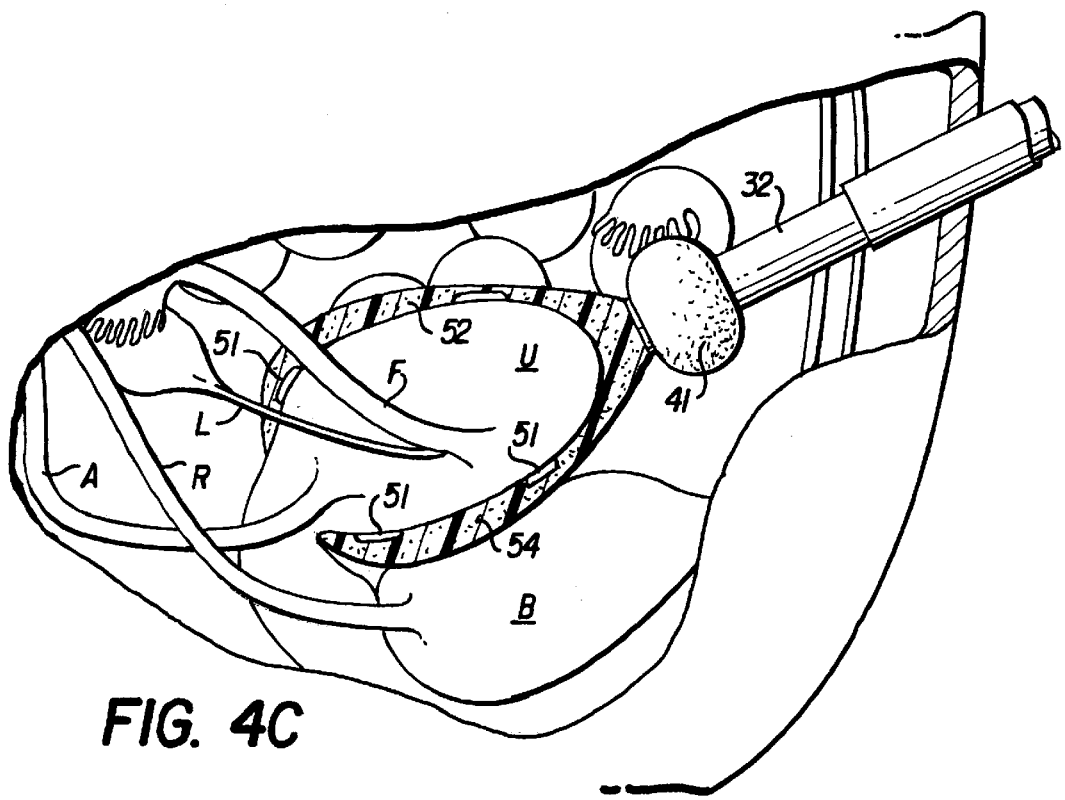
FIG. 4C illustrates the first preferred embodiment in cross-section during use with the protective members.
Figure 4D:
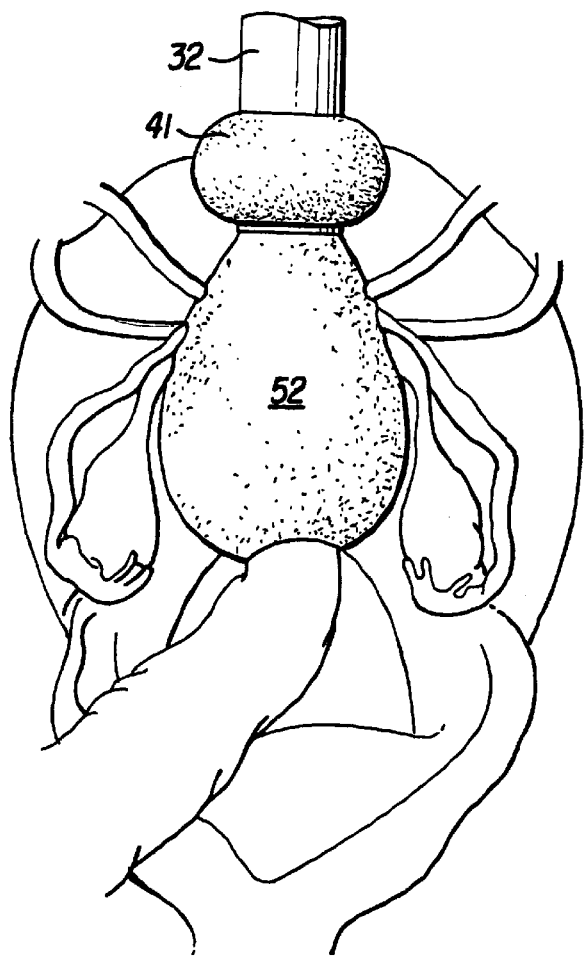
FIG. 4D is a top view of the first preferred embodiment in use.

At this time, protection device 30 is manipulated from the proximal end to position protective members 52 and 54 above the patient's bladder and proximate an outer portion of the fundus of the uterus. This can be accomplished by using protective members 52 and 54 as a blunt dissecting tool, when in the open or closed positions, for lysis of adhesion between the bladder and the uterus at the bladder flap. Handle 44 can then be compressed to a greater degree to provide a large gap between protective members 52 and 54 and lock device 46 can be actuated to fix the position of protective members 52 and 54 relative to one another. Protection device 30 can then be manipulated to cause protective member 52 to pass between the bladder and the uterus, i.e. into the bladder flap, while protective member 54 passes over the uterus. Note that fallopian tubes F, uterine artery A, ovarian ligament L, and other supporting structures can be received in the gap defined between protective members 52 and 54 as illustrated in FIG. 4B. Also ureter R and bladder B are disposed outside of the protective members. Once protective members 52 and 54 are pushed over uterus U, lock device 46 can be released to permit protective members 52 and 54 to approach one another as the surgeon eases compression of handle 44. When uterus U is snugly contained between, and adequately protected by, protective members 52 and 54, lock device 46 can be activated to maintain the relative position of inner member 34 and outer member 32 and thus maintain the position of protective members 52 and 54 around the uterus as shown in FIGS. 4B, 4C, and 4D. In this position, protective members 52 and 54 define a protective cap around uterus U.

Figure 22:
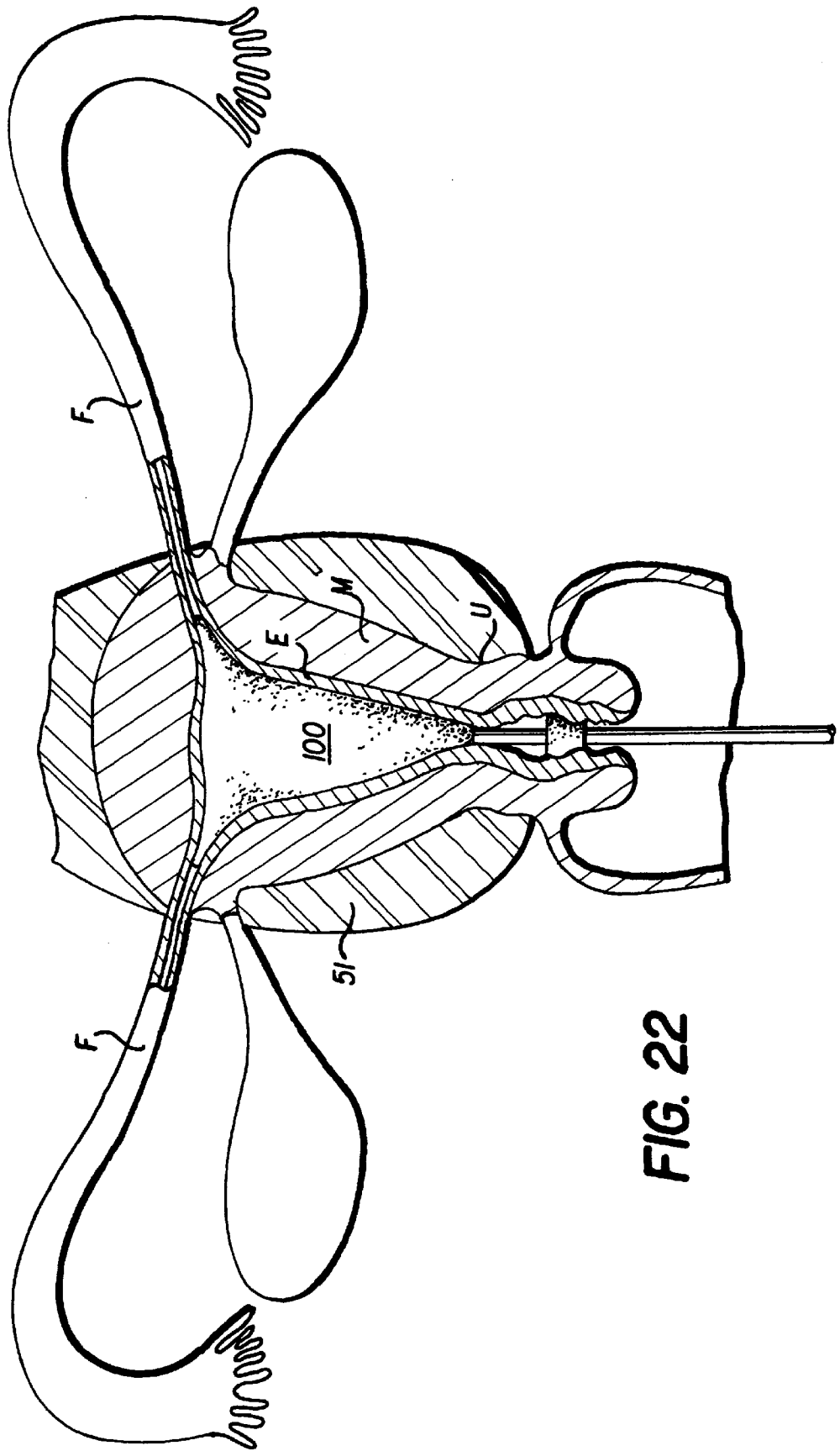
FIG. 22 is a cross-sectional view and the first preferred embodiment in use with an ablation device inserted vaginally into the uterus.

With protective members 52 and 54 secured around the uterus, ablating can be accomplished at high heat for the time required to maintain complete necrosis, of the endometrium or the entire uterus for example, without damaging other organs. For example, as illustrated in FIG. 22, ablating instrument 100, having an expandable member that is inserted vaginally into the uterus, can be use to deliver ablation energy to necrose endometrium E and myometrium M of uterus U while the protective cap is in position around the uterus U. Alternatively, cryogenic ablation, physical scraping, or other procedures can be accomplished without damaging other organs or tissue because the protective cap isolates uterus U. Because the uterine artery, fallopian tubes, ovarian ligament, and other structures pass between insulating members 52 and 54, the ovaries, uterine artery and other tissue and organs are located outside of the protective cap defined by protective members 52 and 54 containing the uterus. Also, care is taken to position the ureters, bowel, and sigmoid outside of the cavity. This is so because protective members 52 and 54 prevent heat or other energy from the uterus from reaching other organs or tissue. Also, the ablating energy can be relatively high to insure that all portions, of the endometrium or the entire uterus for example, even crevices and folds, are necrosed without damage to surrounding organs and other tissue. In the case of heat or other high energy being used for ablation, a cooling fluid can be introduced through one or more of operating channels 38a–38c. The cooling fluid will be absorbed by the sponge material constituting protective covers 58 to lessen the chance that any surrounding tissue is damaged due to heating of insulating members 52 and 54. Any known ablating device can be used to apply the necessary ablating energy. For example, a conventional heating device can be inserted into the uterus vaginally or any of the other devices discussed above can be used. The material used for protective covers 58 can be selected to have the desired isolating properties based on the type of ablation energy.

Temperature sensors 47 can be provided on protective members 52 and 54 and can be electrically coupled to alarm circuit 49 (see FIG. 1) by cable 45. Alarm circuit 49 can effect an alarm, such as a display light, when the temperature of protective members 52 and 54 or of the tissue being ablated is higher than a predetermined temperature that insures the safety of surrounding tissue. Alarm circuit 49 can be coupled to the cooling fluid supply and/or the ablating device to control the temperature in a closed loop manner. For example, when the predetermined temperature is exceeded, the ablating device can be turned off temporarily or the flow of cooling fluid can be increased. Alarm circuit 49 can be a microprocessor based device or other logic circuit.

After ablation has taken place for long enough to ablate the damaged tissue (which can be determined by temperature sensors 47 or other means), the tissue is allowed to cool (in the case of high energy being applied for ablation) and lock device 46 is released and handle 44 is compressed so that protective members 52 and 54 part from one another with a gap defined therebetween that is large enough to permit removal of the protective cap defined by protective members 52 and 54 from uterus U. Cooling time can also be determined by temperature sensors 47. Protection device 30 then can be manipulated to remove protective members 52 and 54 from uterus U. After such removal, handle 44 can be released to a greater degree to press protective members 52 and 54 together and to cause flexible extending arms 56 to move toward the longitudinal central axis so that protective members 52 and 54 are confined within the radial dimensions of outer member 32, as illustrated in FIG. 1. In this state, the distal end of protection device 30 can be removed from the anatomical cavity through the portal sleeve or other small passage. Of course, the ablating device is also removed from the inside of the uterus via the vaginal canal or from any other location through which the ablating device is inserted. The necrosed tissue, whether it be the entire uterus, only the endometrium, or some other tissue, will then shrink over time. However, the patient is spared the psychological trauma associated with removal of a reproductive organ.

Figure 4E:
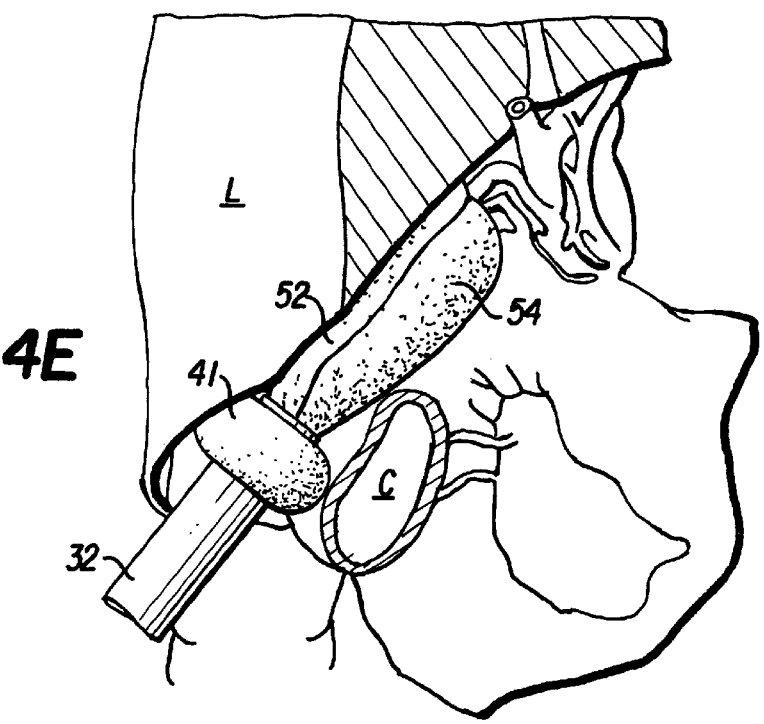
FIG. 4E illustrates the first preferred embodiment with the protective members disposed around the gall bladder.
Figure 4F:
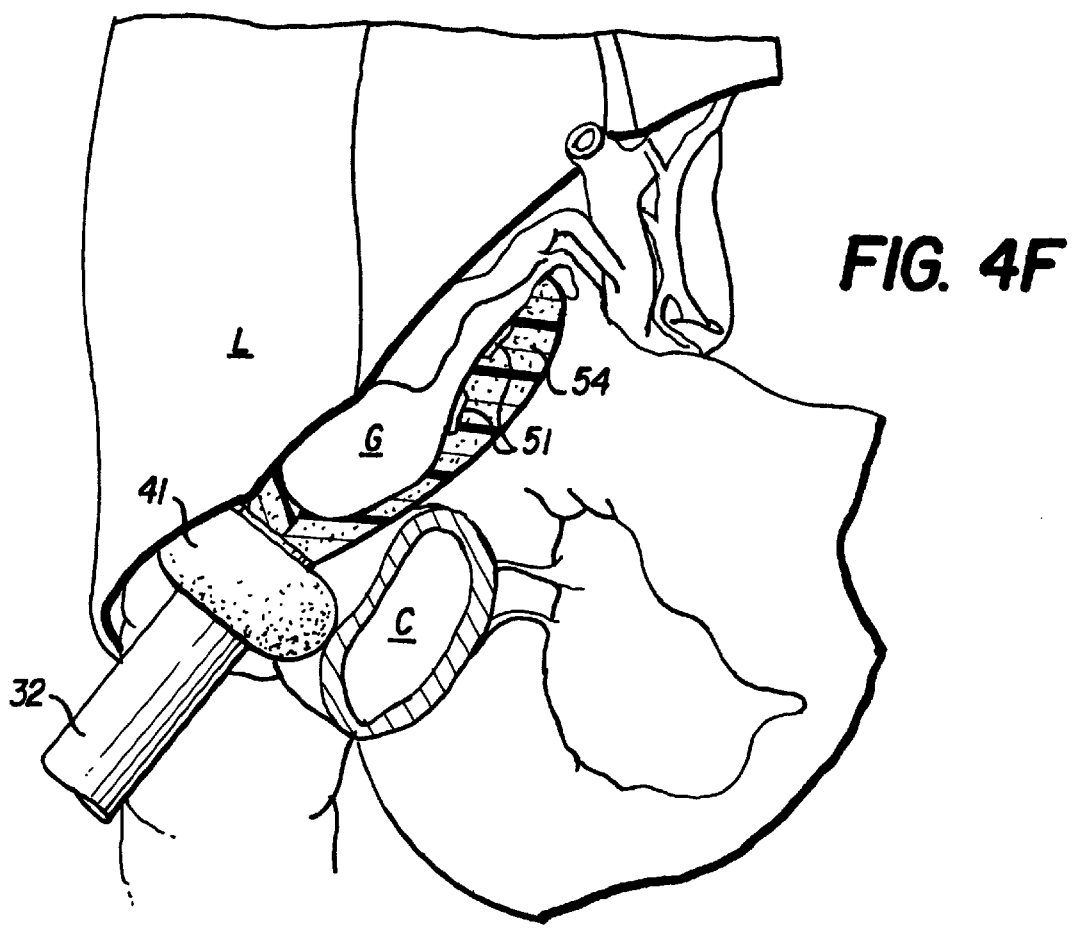
FIG. 4F illustrates the first preferred embodiment with the protective members disposed around a gall bladder and illustrated in cross-section.

The protection device discussed above, is also well suited to facilitate ablating of a diseased gall bladder, FIGS. 4E and 4F illustrate the protective cap covering a gall bladder. In a gall bladder ablation procedure, protective members 52 and 54 are used as a blunt dissecting tool to separate liver L from gall bladder G, in either a partially open position or in the closed position illustrated in FIG. 1 then one of the protective members is inserted between liver L and gall bladder G and the other protective member is inserted between colon C and gall bladder G to separate gall bladder G from liver L and colon C. When protective members 52 and 54 are partially closed around gall bladder G, a protective cap is defined around gall bladder G. In this state, gall bladder G can be ablated, or otherwise manipulated by scraping or the like, without damaging surrounding tissue. Any conventional ablating device can be used to ablate the gall bladder. However, since access to the inside of the gall bladder is not facilitated, an ablating device can be inserted through central channel 39 as instrument 60 (see FIGS. 1 and 2). Alternatively, ablating elements 51, such as heating elements, can be disposed on an inner surface of the protective cap, as shown in FIG. 4F. The appropriate electrical or other type of connections can be provided to apply energy to ablating elements 51. Ablating elements 51 can be positioned for appropriate energy delivery and can be coupled to alarm circuit 49 for control.

Figure 5:
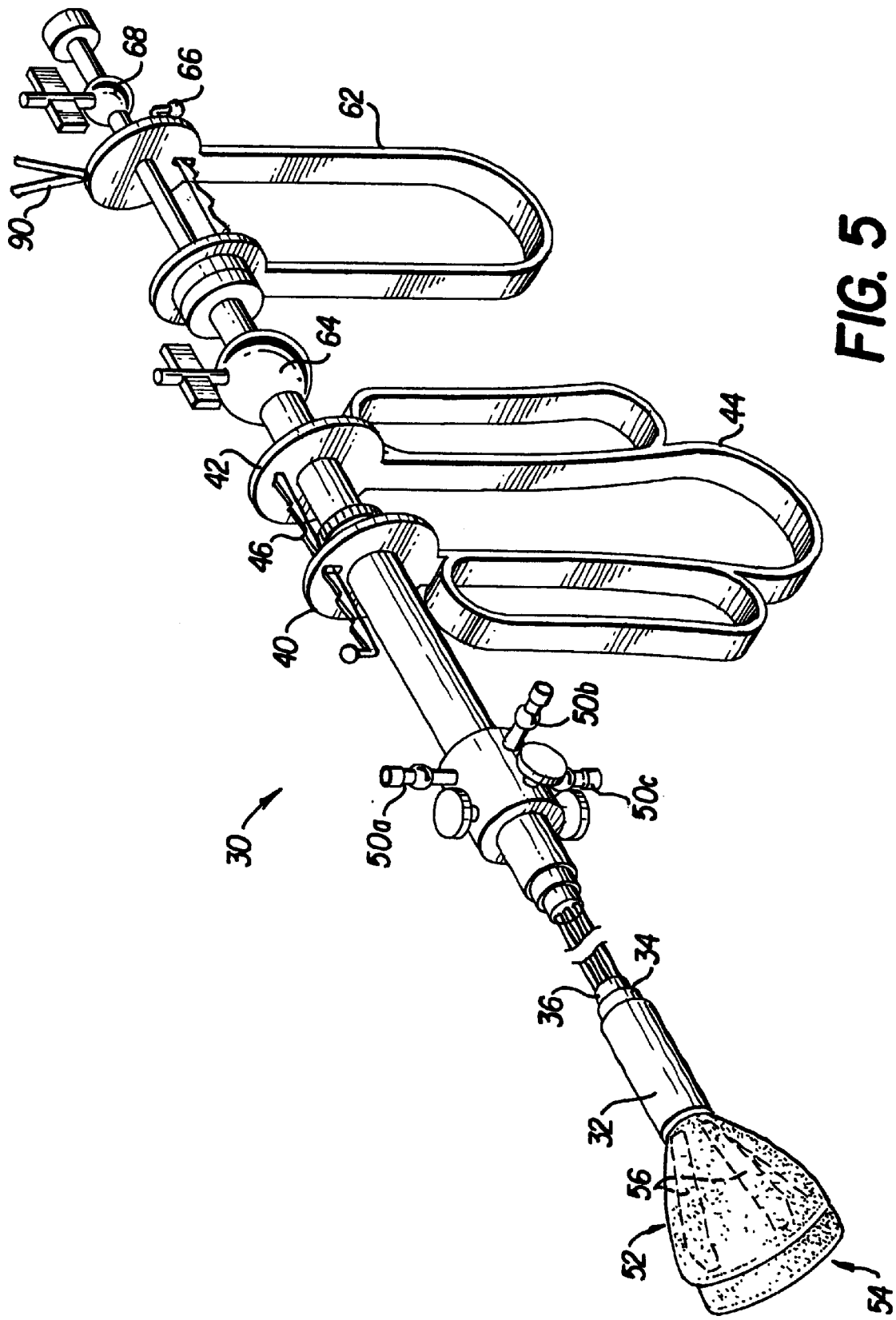
FIG. 5 illustrates a second preferred embodiment.
Figure 6:
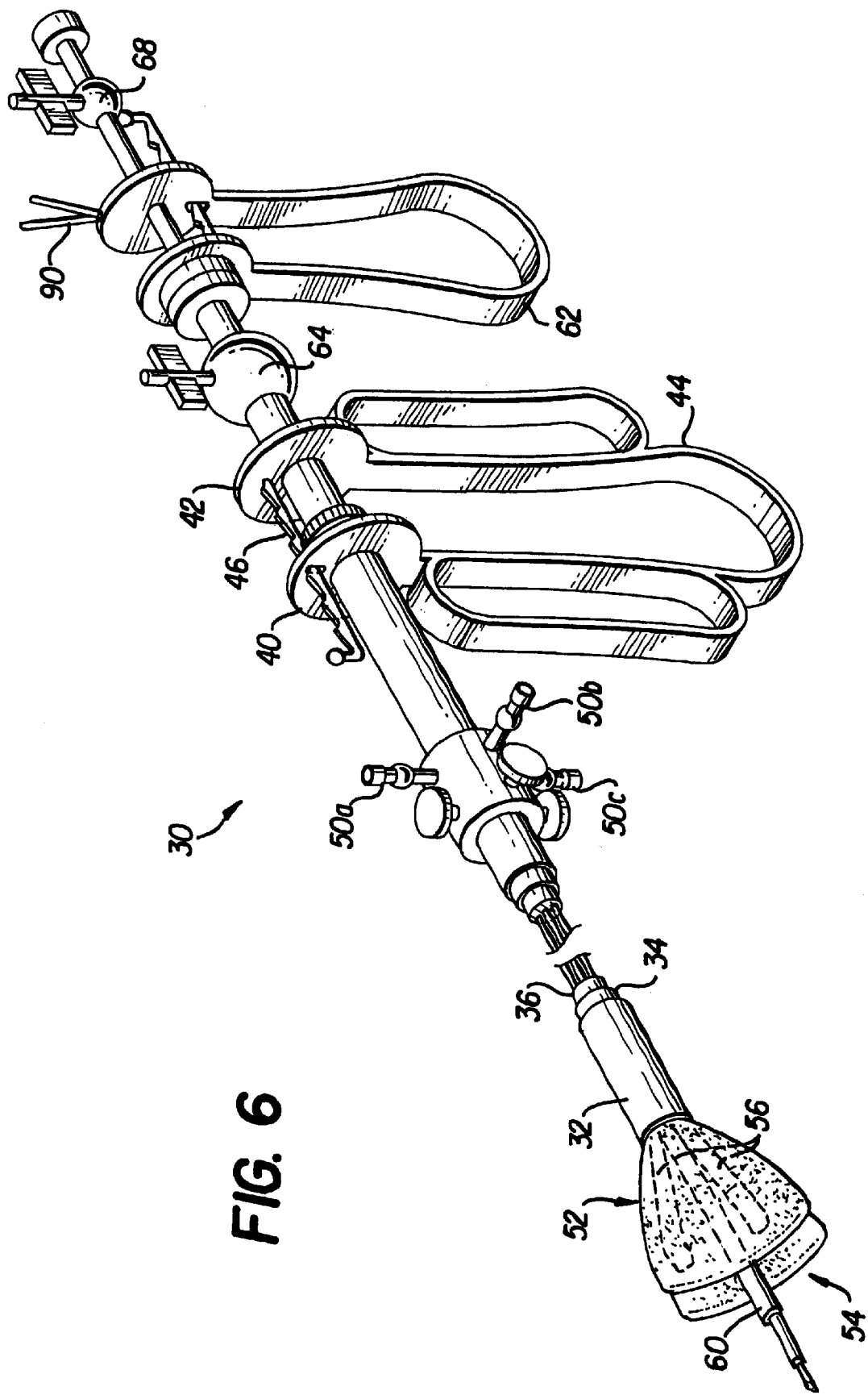
FIG. 6 illustrates the second preferred embodiment with a surgical instrument extending through an operating channel.

A second preferred embodiment of protection device 30 is illustrated in FIGS. 5 and 6. The second embodiment is similar to the first embodiment discussed above and like reference numerals are used to denote similar elements. However, in the second embodiment, protective members 52 and 54 are fan shaped with a slight inward curvature when in the open position illustrated in FIGS. 5 and 6. Flexible extending arms 56 are configured to impart the fan shape to protective members 52 and 54 when handle 44 is compressed. Operation of the second embodiment is similar to the first embodiment. However, protective members 52 and 54 may be more easily placed around irregular shaped or flat organs or other tissue. Also, in the second embodiment, instrument 60 disposed in central lumen 29 has hollow needle 61 as an end effector (which is advanced distally in FIG. 6) for piercing an organ or other tissue to permit the withdrawal of fluid, irrigation, or dispensing of medicaments such as anesthesia, through a hollow channel formed in instrument 60 and port valve combination 68. Of course, instrument 60 can have any appropriate end effector, such as a blade, a clip applicator, or a hook, or instrument 60 can be used for suction, monopolar or bipolar cauterization, or another backup procedure. Protection device 30 of the second preferred embodiment is illustrated with protective members 52 and 54 in the open position. However, protective members 52 and 54 can assume a closed position similar to the first embodiment discussed above when handle 44 is released.

Figure 7:
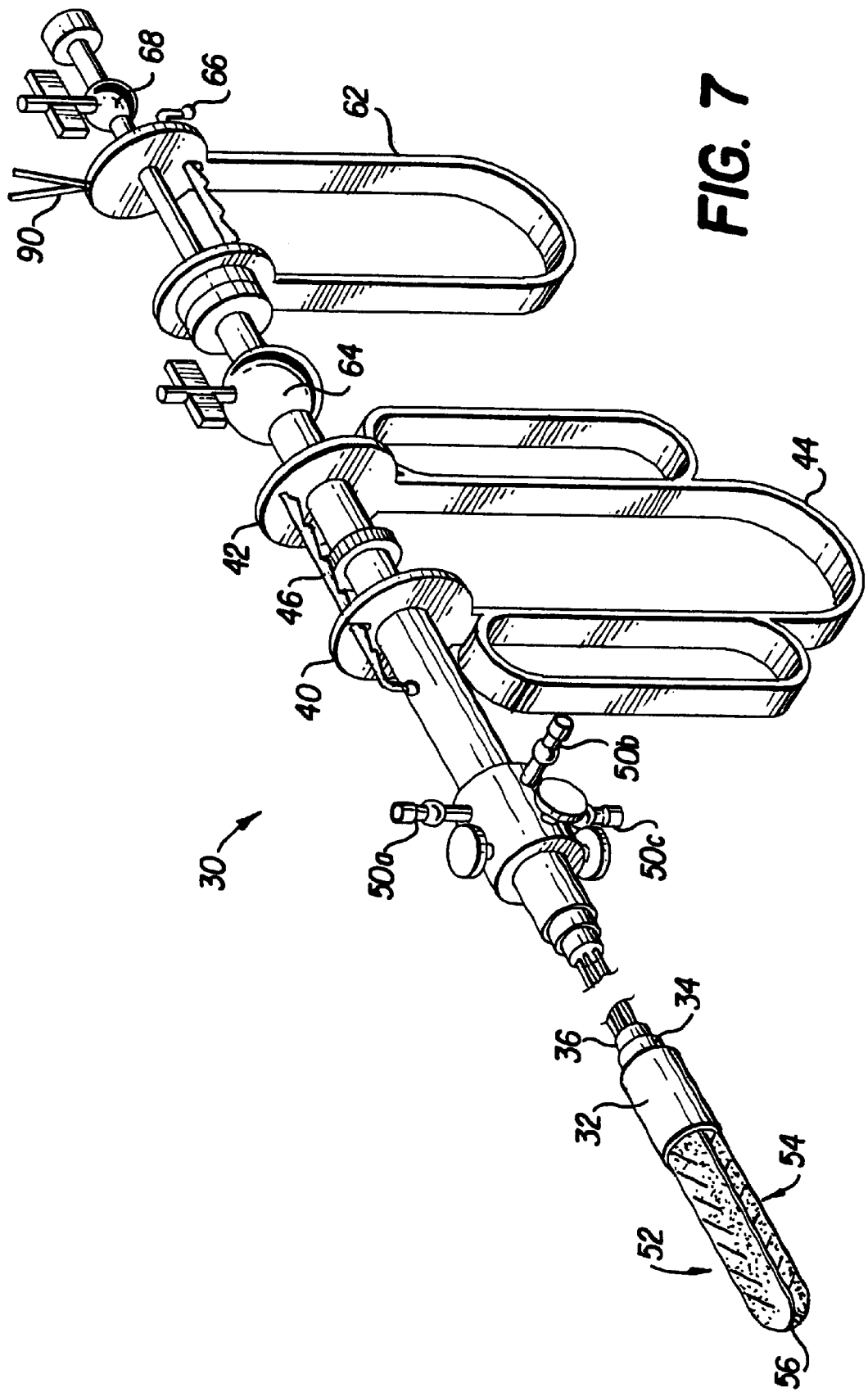
FIG. 7 illustrates a third preferred embodiment with the insulating members in a closed position.
Figure 8:
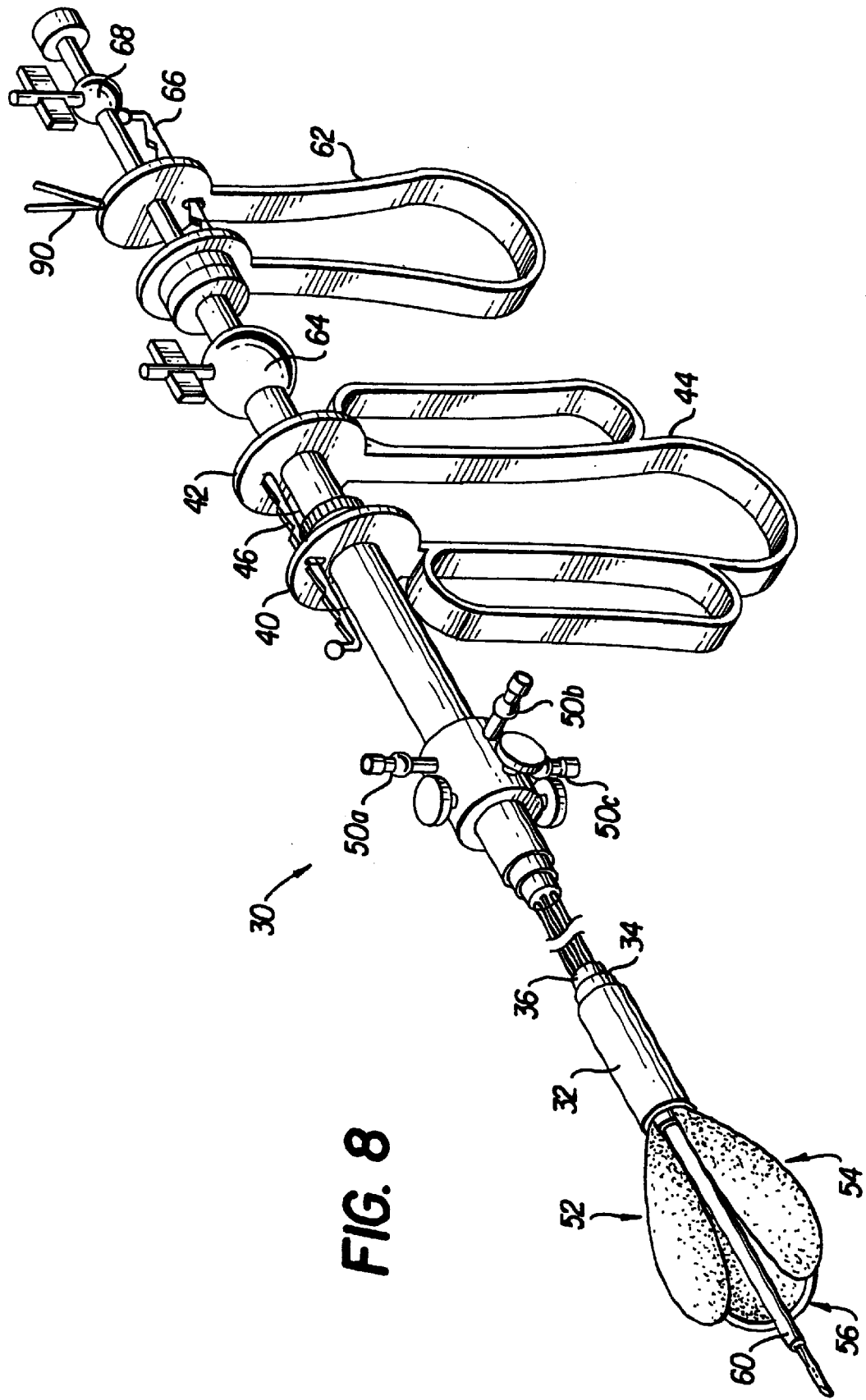
FIG. 8 illustrates the third preferred embodiment with the insulating members in an open position.

A third preferred embodiment of protection device 30 is illustrated in FIGS. 7 and 8. In the third preferred embodiment, there are three protective members 52, 53, and 54 that are of a teardrop shape when open, as illustrated in FIG. 8. In the closed position illustrated in FIG. 7, protective members 52, 53, and 54 are contained within the radial dimensions of outer member 32. Also, other elements of the third embodiment are similar to the first and second embodiments described above. The configuration of the third embodiment provides three slots between protective members 52, 53, and 54 for passage of connecting structures or the like. Also, the use of three protective members 52, 53, and 54 allows larger organs to be covered more completely.

Figure 9:
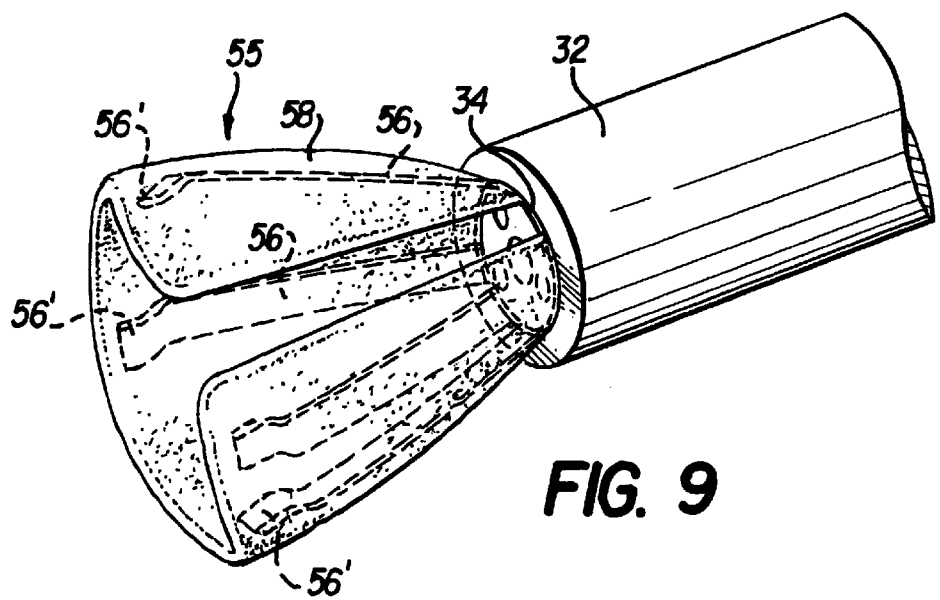
FIG. 9 illustrates a distal end of a fourth preferred embodiment.

A distal end of a fourth preferred embodiment of protection device 30 is illustrated in FIG. 9. In this embodiment, there is a single protective member 55 in a form of a singly cupping that is essentially of a conical shape when in the opened position illustrated in FIG. 9. Flexible extending arms 56 each have an inwardly offset portion 56' to partially close the open end of the cone formed by protective member 55. This permits protective member 55 to wrap around an organ more completely. A single slot is formed in protective member 55 when opened to permit connecting ligaments, blood vessels, or the like to pass therethrough when protective member 55 is placed over an organ. Other elements of the fourth preferred embodiment are similar to the embodiments discussed above. For example, an instrument having a needle or another appropriate end effector can be inserted through central lumen 29. Also, protective member 55 can be moved to a closed position by advancing outer member 32 with respect to inner member 34.

Figure 10:
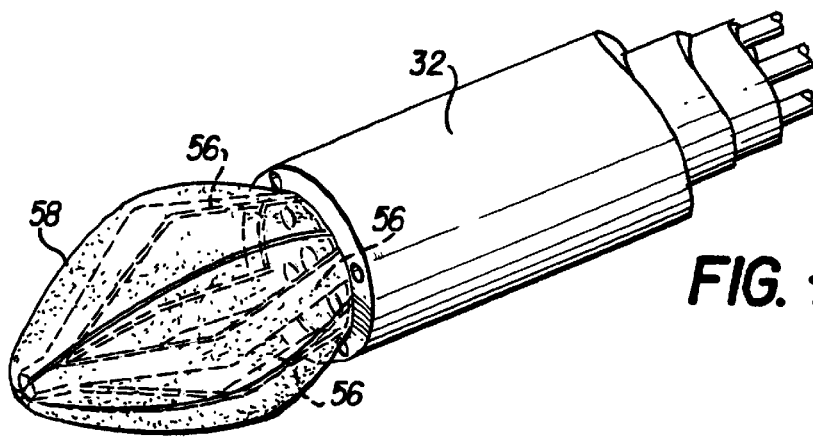
FIG. 10 illustrates a distal end of a fifth preferred embodiment with the protective members partly closed.
Figure 11:
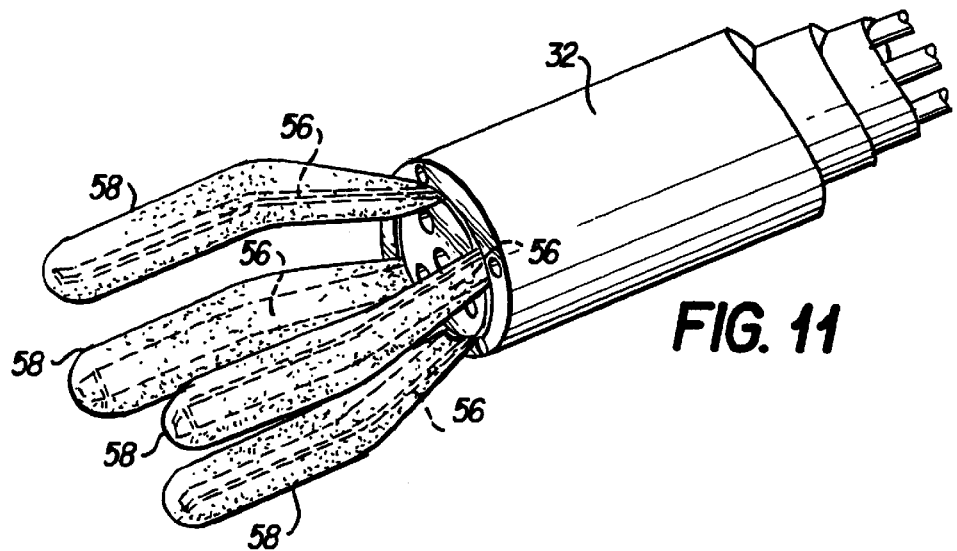
FIG. 11 illustrates the distal end of the fifth preferred embodiment with the protective members open.
Figure 12:
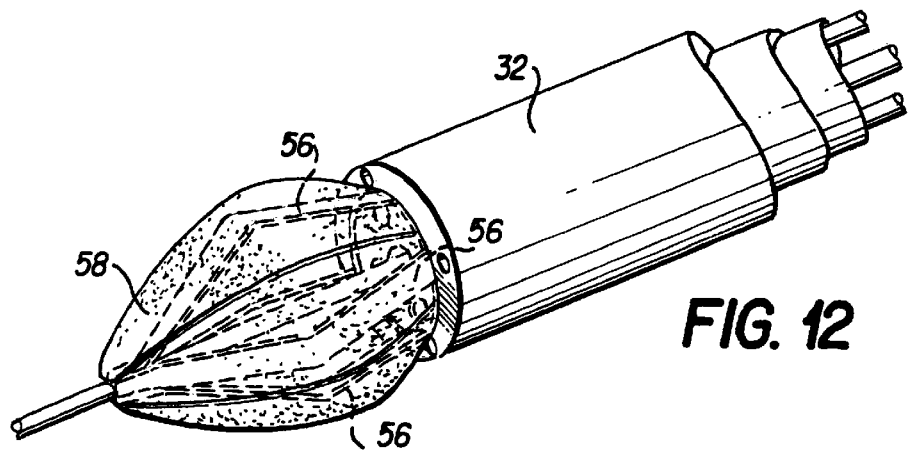
FIG. 12 illustrates the distal end of the fifth preferred embodiment with a surgical instrument extending through an operating channel.

A fifth preferred embodiment is illustrated in FIGS. 10–12. A plurality of plate-like flexible extending arms 56 each have protective covers 58 forming cupping elements thereon to define a plurality of elongated strip-like protective members 57. When in the entirely closed position, protective members 57 are accommodated within the radial dimensions of outer member 32, similar to the other embodiments discussed above. When entirely opened, protective members 57 extend distally and outward to define gaps between adjacent protective members 57 as illustrated in FIG. 11. After being placed around an organ or other tissue, protective members 57 can be closed partially, to the position illustrated in FIG. 10, to surround the organ or tissue. Ligaments, blood vessels, or other connecting tissue can extend between adjacent protective members 57. Since there are a plurality of protective members 57, there are many spaces between protective members 57 through which connecting tissue can extend while allowing an organ to be covered adequately to protect adjacent tissue from damage during an ablating process, or other process.

As illustrated in FIG. 12, an instrument having an end effector, such as solid needle 62, can be inserted through central lumen 29 to perform an operation on tissue, prior to, after, or during ablating. Solid needle 62 can be extended distally beyond insulating members 57 when insulating members 57 are open, closed entirely, or partially closed as illustrated in FIG. 12. Also, an ablating instrument can be inserted through central lumen 29 in place of needle 62.

Figure 13:
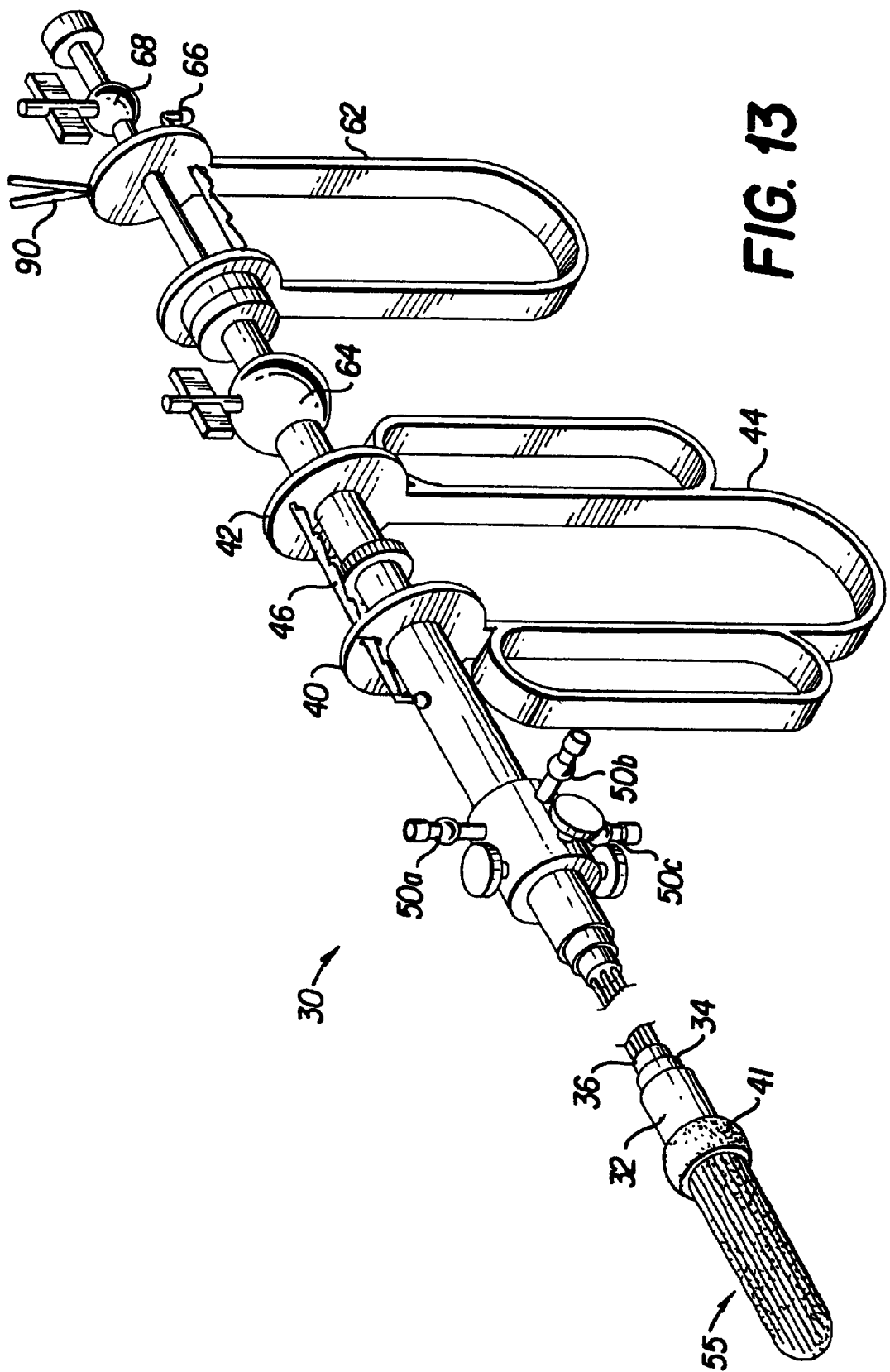
FIG. 13 illustrates a sixth preferred embodiment with the protective member closed.
Figure 14:
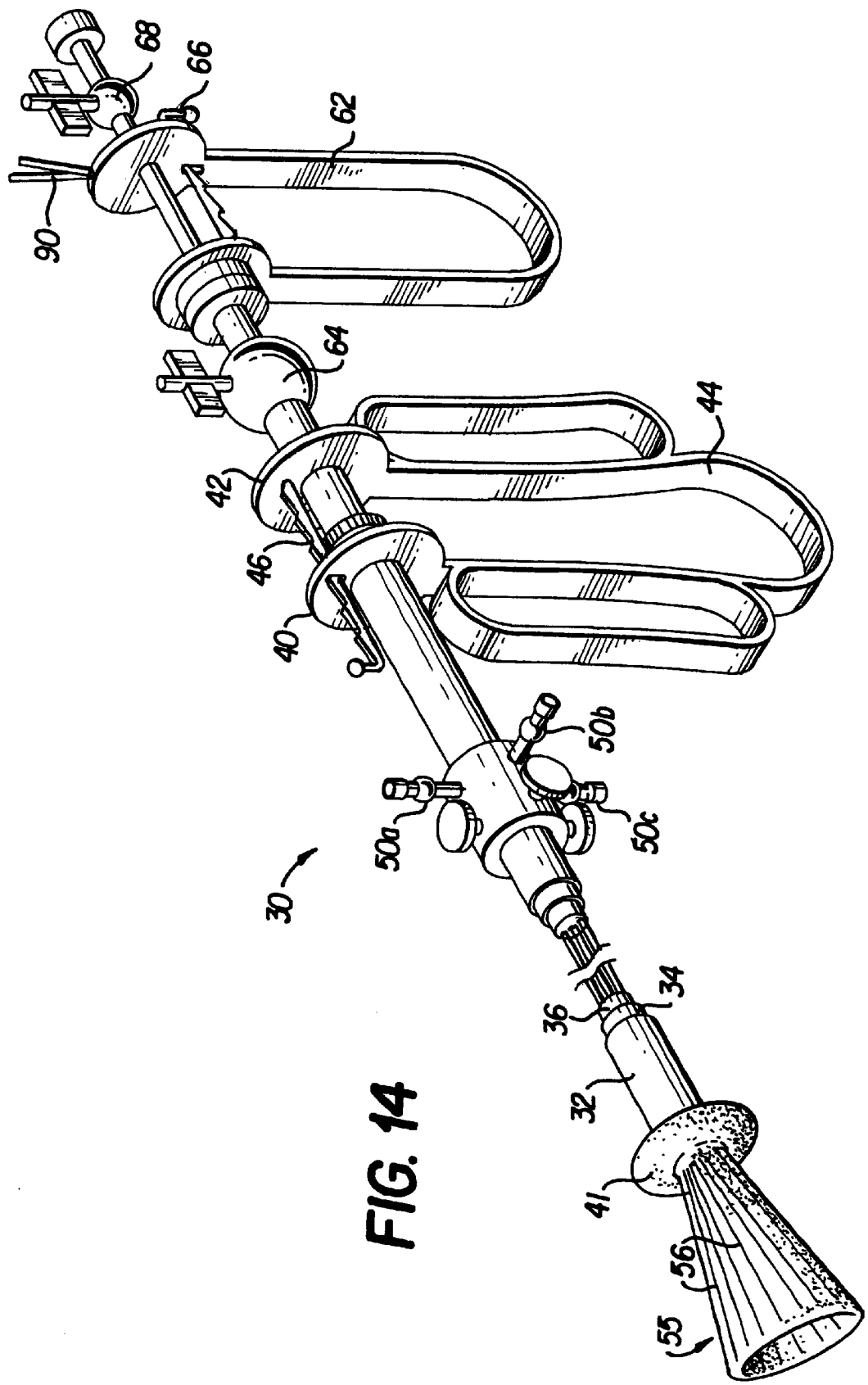
FIG. 14 illustrates the sixth preferred embodiment with the protective member open.

FIGS. 13 and 14 illustrate a sixth preferred embodiment having a single protective member 55 that is conical when in the opened position illustrated in FIG. 14. When handle 44 is compressed, outer member 32 slides proximally to permit flexible extending arms 56 to extend radially and distally similar to the embodiments discussed above. Protective cover 58 is stretched around all of extending arms 56 to define an uninterrupted conical protective member 55 when extending arms 56 are in the open position. When handle 44 is released and outer member 32 is biased distally over a portion of flexible extending arms 56 by the resilient force of handle 44, protective member 55 assumes the closed position illustrated in FIG. 14 in which flexible extending arms 56 extend essentially parallel to one another.

Figure 15:
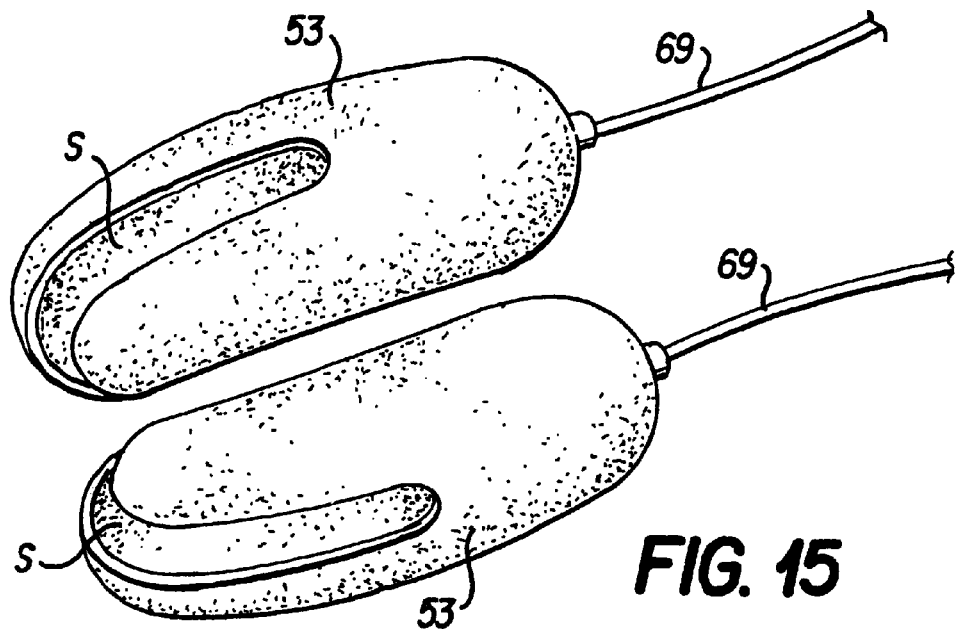
FIG. 15 illustrates the insulating member of a seventh preferred embodiment.

A seventh preferred embodiment of the invention is illustrated in FIG. 15. Two protective members 53 formed as cupping elements are each of an extended U-shaped configuration. Slot S is defined in each protective member 53 to accommodate an organ or other tissue that is to be covered. Protective members 53 can be formed of a nonporous material to define a bladder or can be made of a porous material, such as a sponge material. Hose 69 is coupled to each protective member 53 to provide a cooling fluid, anesthesia, or medicaments to an interior of protective members 53. In the case of porous protective members 53, the fluid will pass through the outer surface of protective member 53. Of course, in such a case, the fluid must be biocompatible. Separate suction means can be provided to remove excess fluid. In the case of nonporous protective members 53, cooling is accomplished by the cooling fluid which remains inside protective member 53.

In use, each protective member 53 is placed over an organ, such as the uterus, with a portion of the organ received in each slot S. Fallopian tubes, the broad ligament, or other connecting structures, can pass through the sides of slots S or through a gap between each protective member 53. After protective members 53 are applied to the organ, either by an endoscopic device, laparoscopic device, open surgical device, or the like, ablation of the organ can be accomplished by a conventional ablating device or by an ablating device incorporated into protective members 53. Cooling fluid can be introduced to protective members 53 as needed from an external fluid source coupled to the proximal end of hose 69. Of course, one hose 69 can be coupled to both protective members 53 by a Y-adaptor, or more than one hose 69 can be coupled to each protective member 53, as needed. There can be only one or more than two protective members 53, as needed to adequately cover the organ being ablated. Protective members 53 can be applied to the organ by an endoscopic device or other means. This embodiment is also well suited for use during ablating of flat organs or tissue, such as lobes of the liver.

Figure 16:
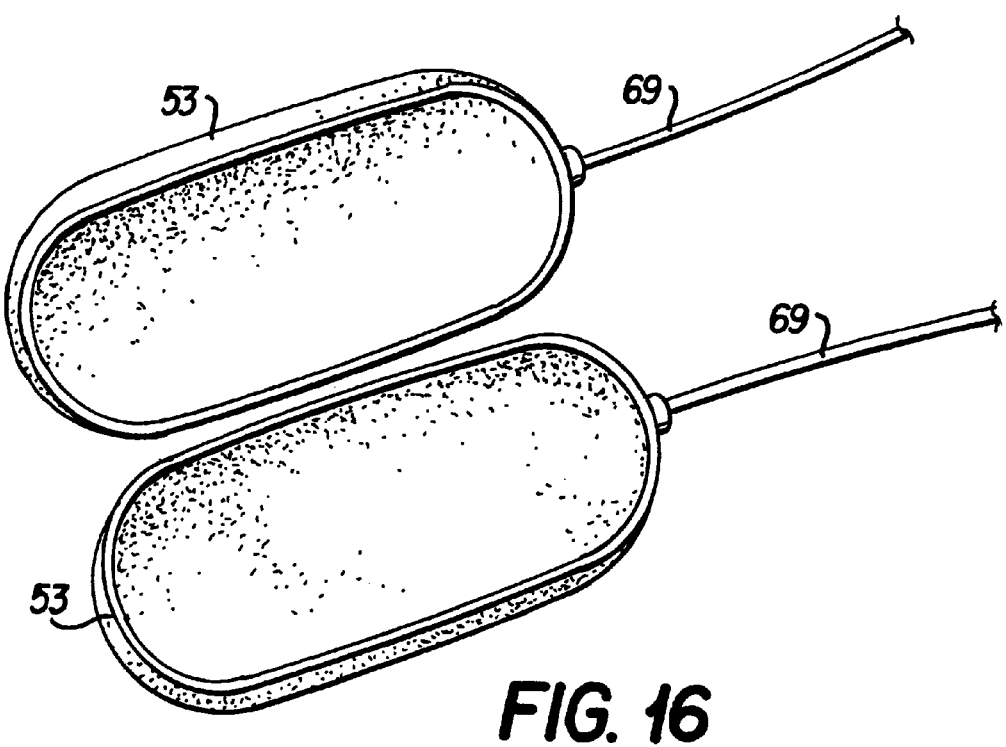
FIG. 16 illustrates a modification of the seventh preferred embodiment.

A modification of the seventh embodiment is illustrated in FIG. 16. In this modification, protective members 53 or cupping elements are trough shaped and can be applied respectively above and below a particular tissue portion or organ, the uterine fundus for example, to protect surrounding tissue during ablation. Other details of this modification are similar to the seventh embodiment described above. This modification is also adapted to use on the gall bladder to isolate the gall bladder from surrounding tissue and organs, such as the liver, to protect the surrounding tissue and organs. Of course surrounding organs can be dissected retracted and manipulated to permit protective members 53 to be placed around the organ.

Figure 17:
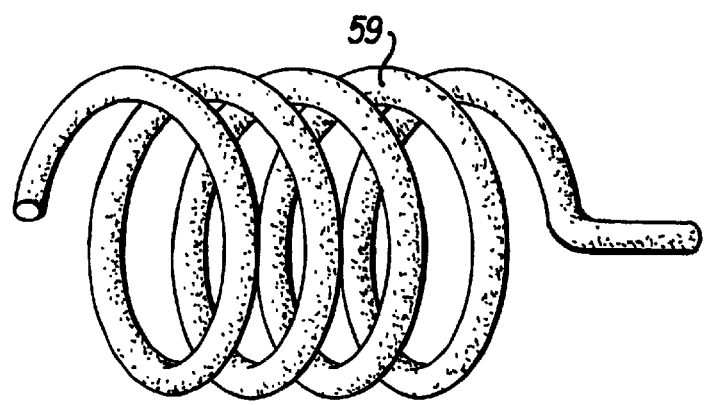
FIG. 17 illustrates the protective member of an eighth preferred embodiment.

An eighth embodiment of the invention is illustrated in FIG. 17. Protective member 59 is in the form of an elongated strip or tube that can be wrapped around the organ to be ablated to isolate surrounding tissue from the ablation energy and to protect the surrounding tissue. Protective member 59 can be made of a resilient or shape memory material that naturally is coiled or of a flexible material that does not hold any particular shape. Protective member 59 can be secured in place through known clips, sutures, or other means. Of course, protective member 59 can be made of any porous or non porous biocompatible material and can define a cavity therein. In the case of protective member 59 being of a porous material or having a cavity defined therein, cooling fluid, anesthesia, or the like can be supplied to an interior of protective member 59 as in the embodiments described above. Protective member 59 can be applied to the tissue either by an endoscopic device, laparoscopic device, culdescopic device, culpescopic device, open surgical device, or the like, and ablating of the organ can be accomplished by any conventional ablation device or an ablation device incorporated in protective member 59. Further, protective member 59 is particularly suited to insulating a uterus, in which case the broad ligament and fallopian tubes extend between successive wraps and the bladder is separated from the uterus before wrapping protective member 59, or the gall bladder, in which case the liver must be separated from the gall bladder before wrapping protective member 59. Further, the eighth embodiment can be used to wrap fallopian tubes, ovaries, or other elongated or irregularly shaped tissue that is to be ablated to protect surrounding tissue.

Figure 18:
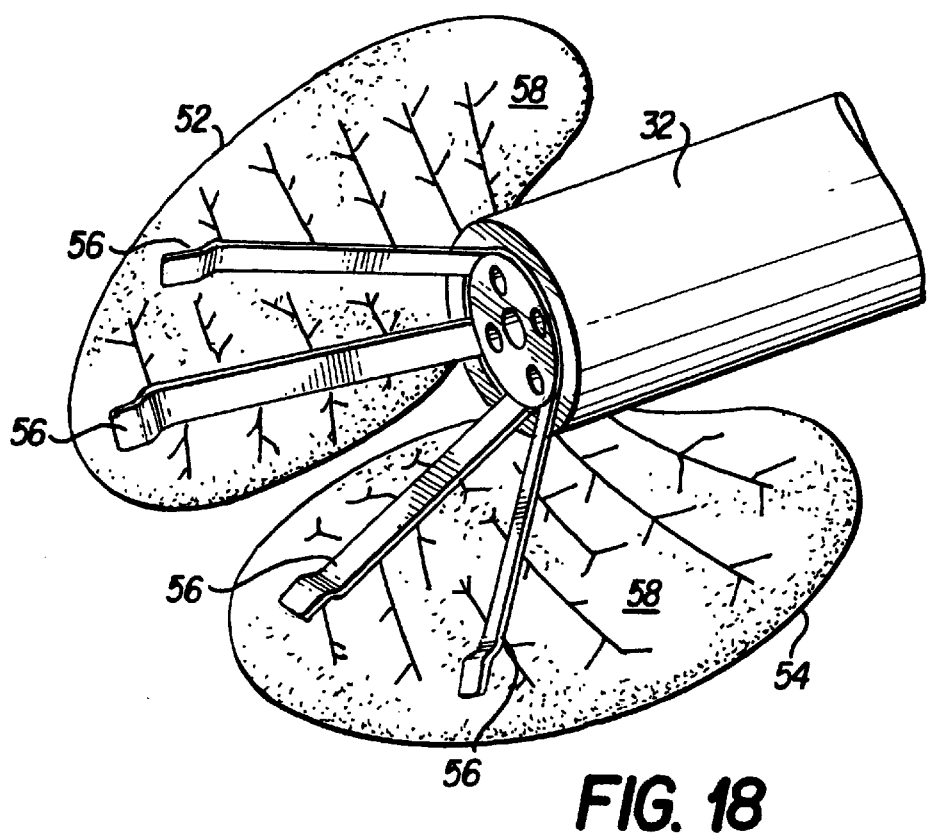
FIG. 18 illustrates the distal end of a ninth preferred embodiment.

FIG. 18 illustrates a distal end of a ninth embodiment of the invention. In this embodiment, protective members 52 and 54 or cupping elements are oval-shaped and are disposed at an acute angle with respect to one another when in the illustrated open position. Because edges of protective members 52 and 54 extend beyond arms 56, it may be desirable to use a more rigid material for protective covers 58 or reinforcing members in protective members 52 and 54. Other elements of this embodiment are similar to the first through sixth embodiments.

FIGS. 19 and 20 illustrate an alternative set of handles that can be used in place of handle 44 and/or handle 62 discussed above. Handles 92 and 94 are scissor like and can be pressed together to cause outer member 32 to move relative to inner member 34 thus opening and closing the protective members. Handles 92 and 94 are pivotally mounted in housing 79. By pressing button 66, handles 92 and 94 are disengaged from outer member 32 and can be rotated in concert to any desired orientation.

Figure 21A:
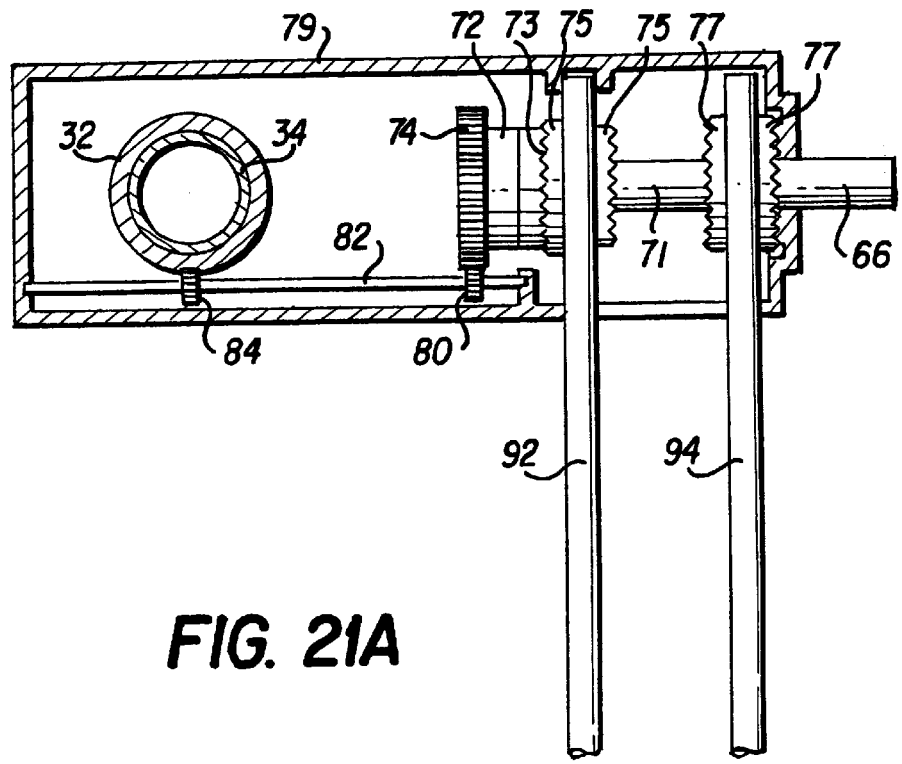
FIGS. 21A and 21B are cross sectional views of the alternative handle arrangement taken along line 20—20 of FIG. 19.
Figure 21B:
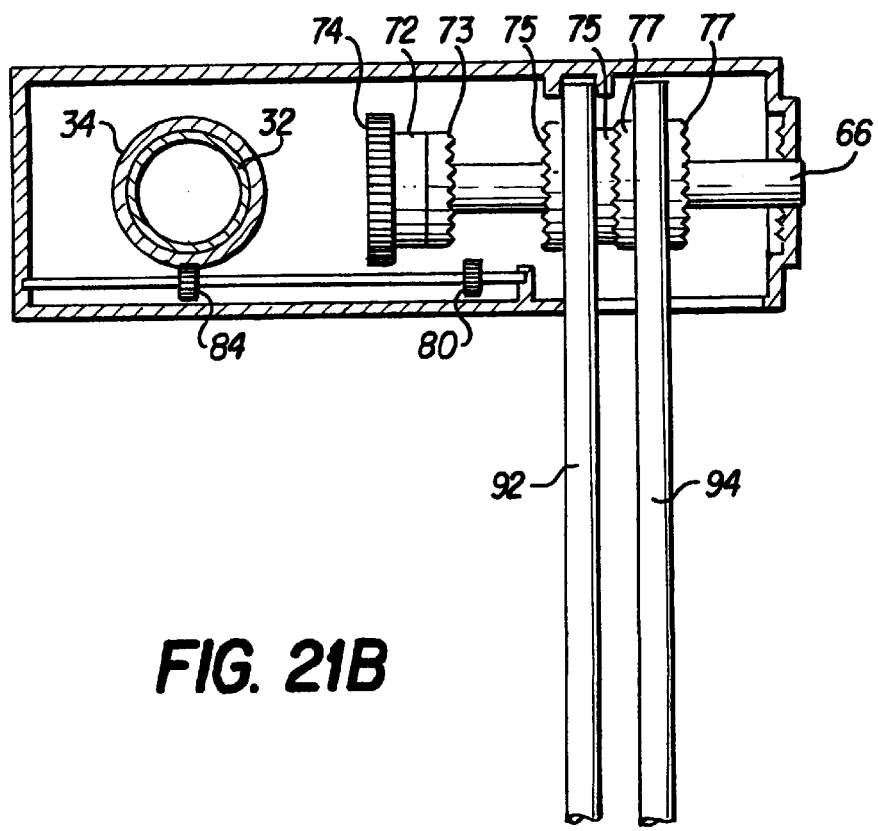

FIGS. 21A and 21B illustrate the internal mechanism coupling handles 92 and 94 to outer member 32. Operating member 72 is rotatably disposed on shaft 71 and has gear portion 74 that is engaged with gear 80 on shaft 82. Gear 84, also disposed on shaft 82, is engaged with a rack formed on outer member 32. Operating member 72 is fixed axially on shaft 71 and has radially extending serrated teeth 73 formed on a side opposite gear portion 74.

Handle 92 is also rotatably mounted on shaft 71 and is slidable relative to shaft 71. Handle 92 is fixed in axial position by projections formed on an inner surface of housing 79. Handle 92 has radially extending serrated teeth 75 on each side thereof at a top portion that is disposed around shaft 71. Shaft 71 is normally biased to the right in FIG. 20A by a spring (not shown) to press serrated teeth 73 into engagement with serrated teeth 75 thus fixing the relative position of operating member 72 and handle 62. Handle 94 is rotatably mounted on shaft 71 and fixed axially on shaft 71. Radially extending serrated teeth 77 are formed on each side of handle 64 at a top portion that surrounds shaft 71 and serrated teeth 77 are normally biased by spring 76 into engagement with teeth formed on an inner surface of housing 79 to fix the position of handle 94 with respect to housing 79. In this state handle 92 is coupled to outer member 32 and handle 94 is fixed in position. Pressing handle 92 towards handle 94 will cause outer member 32 to move away from the protective members to open the protective members as described above.

Release of handles 92 and 94 causes the insulating member to return to the closed position due to the resilient bias of the flexible extending arms. Lock protrusions 65 and 67 (see FIG. 19) are disposed on handles 92 and 94 respectively and are serrated to interlock and allow the position of handles 92 and 94 to be maintained in a state corresponding to a desired position of the insulating member. Lock protrusions 65 and 67 can be pivoted to a position at which they will not interlock if desired. Additionally, handles 92 and 94 can be biased apart or outer member 32 can be biased distally or proximally, depending on desired operating characteristics. Further, the handles can be biased either apart or together.

When shaft 71 is pressed to the left, as illustrated in FIG. 21B, by depressing button 66, serrated teeth 77 engage serrated teeth 75 to fix the relative positions of handles 92 and 94 and serrated teeth 73 are disengaged from serrated teeth 75 to disengage handle 92 from outer member 32. This permits the set of handles 92 and 94 to be rotated in concert, as indicated by arrow A in FIG. 18, to the desired orientation without affecting the state of the insulating member. This permits the surgeon to adjust the handles to a comfortable orientation.

Inner member 34 can be constructed to permit the protective members to be drawn completely into outer member 32. In this state, sponge 41 can be used as a blunt dissecting tool between two pieces of tissue for lysis of adhesion between the tissue pieces. This procedure facilitates inserting the protective member between certain tissues that tend to adhere to one another.

From the above, it is clear that the invention permits an organ or other tissue to be heated, cooled, scraped, or otherwise manipulated during ablating without damaging surrounding tissue by placing a protective cap around the organ or other tissue. This permits the ablating energy to be high enough to cause complete necrosis in the desired tissue or organ, including hard to reach crevices defined by folds or the like. Therefore, ablation can be complete and reliable. The invention can be used to treat endometriosis of the uterus or damage to other organs or tissue, such as the gall bladder, fallopian tubes, or ovaries. For example, when the protective cap of the invention is utilized during ablation of the uterus, the entire endometrium as well as the myometrium can be necrosed without damaging surrounding tissue. This ensures that the endometrium, usually the source of problems, is entirely necrosed.

The insulating members can be proportioned and shaped in any appropriate manner to isolate the organ or tissue which is to be ablated. The insulating members can be movable between open and closed positions or fixed in a desired position. The protective cap defined by the insulating members can be adjustable in size by moving the arms in the manner discussed above. Also, because the insulating members can be resilient, the protective cap can easily deform (e.g., expand and contract) to adjust to organs of various sizes and shapes. For example, the protective cap can be adjusted to conform to a uterus that is misshapen because of fibroids. Further, the protective members can be applied to the organ endoscopically, laparoscopically or through open surgery.

Any type of ablating method can be used in combination with the invention. For example, heat, laser, electromagnetic radiation, ultrasonic radiation, cryogenic, RF, or mechanical scraping ablating devices can be used. In particular, examples of ablation energy that can be used include electrical energy (including RF energy, unipolar cauterization, bipolar cauterization, and electric heating elements), radiated energy such as microwaves, laser energy such as an Nd:YAG laser, cold fluid treatment, such as liquid $N_2$, externally heated fluid treatment, exothermic chemical reactions, exothermic nuclear reactions, photodynamic energy, acoustic energy such as ultrasonic energy, other radiated electromagnetic energy and chemical wash treatments.

The preferred embodiments illustrate endoscopic insertion. However, the protective cap of the invention can be inserted culdoscopically, culposcopically, or in any other minimally invasive or conventional manner. In the case of culdoscopic or culposcopic insertion, the protective cap can have an umbrella-type configuration, with the umbrella being opened after insertion and pulled back over the uterus or other organ to isolate the organ.

Additionally, ablating energy, such as heat, can be generated by the protective cap by transducers, such as heating coils, ultrasonic transducers, or the like disposed inside the protective cap. Monitoring transducers, such as temperature sensors, can be provided in the protective cap to monitor and control the ablation process. Appropriate energy transmission elements, such as electric conductors or fiber optic elements, can be disposed in the instrument. Various energy transmission elements and measurement sensors can be disposed on the protective cap to transmit energy for ablation and to monitor/control the ablation procedure. The quantity, type, and arrangement of these elements and sensors can be determined based on the type and size of tissue being ablated, surrounding tissue, and other practical factors.

Further, an anesthetic agent, such as Marcain™, or Lidocaine™ can be impregnated in the protective cap or any other element of the invention to minimize pain while avoiding general anesthesia. Alternatively, the anesthesia can be supplied to the protective cap through a tube, operating channel, or the like. The various components of the invention can be made of known biocompatible materials for disposal after use or for reuse. For example, the protective covers can be made of known biocompatible sponge materials, in which case they may be disposed of after each use. The protective covers can be supported by flexible arms and can be attached to the flexible arms by any known means, such as a pocket formed in the protective covers for receiving the flexible arms.

Any appropriate mechanical linkages can be used to cause the relative movement between the inner and outer members. For example, two movable handles can be scissor mounted or one handle can be pivotally mounted. Various gears, racks, or other components can be used to transfer motion from the handles to the other members of the device. Further, the protective members can be moved between open and closed positions by means other than relative movement between an inner and outer member, such as pivots or the like. Any appropriate structure can be used to lock or bias the insulating members into the desired open or closed positions.

The protective members can be of any structure that provides the desired protection. For example, instead of a flexible cover over flexible semi-rigid arms, the protective cover can be made of a rigid or semi-rigid material, such as plastic or rubber. Alternatively, in the case of protection from electromagnetic radiation, the protective members can be metallic or have a metallic component.

Electrical connector 90 can be used to couple surgical instrument 60 to an electric power source to permit surgical instrument 60 to be used for unipolar or bipolar cauterization. Of course the cauterizing electrodes must be properly electrically insulated from other elements by the insulating tube or other insulating members. The surgical instrument can be an ablating device to permit single puncture procedures.

Various additional instruments can be introduced into the anatomical cavities through channels defined in the protection instrument or through separate structure sites to assist in manipulation of tissue for the protected ablation procedure or for other procedures. Such additional instruments include blunt or sharp dissecting instruments, scissors, biopsy specimen instruments, forceps, suturing instruments, suction instruments, cutting instruments, clip applicators, ring applicators, coagulating instruments, cautery instruments, sponge sticks, and the like.

Visualization of the procedure can be accomplished with an endoscope or other imaging instrument inserted through the protective instrument or through a separate puncture. Also, visualization can be accomplished with a noninvasive device, such as an X-ray machine.

The invention can be used in endoscopic procedures by being inserted through a portal sleeve disposed in an aperture formed in the patient's body or can be inserted through an open incision. Finally, the various features of the different embodiments can be combined. For example, each embodiment can have a cooling fluid tube or an instrument inserted through a central channel.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A surgical tissue protection device comprising:
    an elongated body having a distal end adapted to insertion into an anatomical cavity and a proximal end adapted to manipulation from outside of the anatomical cavity; and
    a cupping element disposed on said distal end and being sized and adapted to substantially envelope anatomical tissue inside the anatomical cavity, the cupping element operative to move to and between a closed state and an opened state, wherein, in the closed state, the distal end of the elongated body is inserted into the anatomical cavity and, in the opened state, the cupping element in the anatomical cavity receives the anatomical tissue so that the cupping element can move towards the closed state to substantially envelope the anatomical tissue.

2. A device as recited in claim 1, wherein said elongated body comprises a tubular inner member disposed at least partly inside a tubular outer member, said outer member being slidable with respect to said inner member.

3. A device as recited in claim 2, wherein said protective cap is disposed on a distal end of said inner member.

4. A device as recited in claim 3, wherein said protective cap comprises at least one protective member.

5. A device as recited in claim 4, wherein said at least one protective members each comprise a cover disposed on at least one flexible arm extending from a distal end of said inner member.

6. A device as recited in claim 5, further comprising:
   means for causing relative sliding movement of said outer member with respect to said inner member, movement of said outer member distally over said inner member causing said flexible arms to move toward a central longitudinal axis of said device to permit said protective members to move between an open position, wherein said insulating members extend beyond radial dimensions of said outer member, and a closed position wherein said insulating members are contained essentially within the radial dimensions of said outer member.

7. A device as recited in claim 6, wherein said protective members are spoon shaped when in the open position.

8. A device as recited in claim 1, wherein said protective cap comprises at least one protective member, said at least one protective members each comprise a cover disposed on at least one flexible arm extending from a distal end of said elongated body.

9. A device as recited in claim 1, further comprising:
   at least one operating channel defined in said inner member.

10. A device as recited in claim 1, further comprising:
    a surgical instrument movably disposed in an operating channel.

11. A device as recited in claim 1, further comprising energy transmission elements disposed on said protective cap.

12. A device as recited in claim 1, further comprising energy sensors disposed on said protective cap.

13. A surgical tissue protection device comprising:
    an elongated body having a distal end adapted to insertion into an anatomical cavity and a proximal end adapted to manipulation from outside of the anatomical cavity, said elongated body comprising a tubular inner member disposed at least partly in a tubular outer member, said outer member being slidable with respect to said inner member;
    a plurality of protective members disposed on said distal end and being adapted to substantially cover anatomical tissue inside the anatomical cavity, each of said protective members comprising a protective cover disposed on at least one flexible arm extending from a distal end of said inner member; and
    means for causing relative sliding movement of said outer member with respect to said inner member, movement of said outer member distally over said inner member causing said at least one flexible arm to move toward a central longitudinal axis of said device to permit said protective members to move between an open position, wherein said protective members extend beyond radial dimensions of said outer member, and a closed position, wherein said insulating members are contained essentially within the radial dimensions of said outer member.

14. A device as recited in claim 13, wherein said protective members are spoon shaped when in the open position.

15. A device as recited in claim 13, further comprising:
    at least one operating channel defined in said inner member.

16. A device as recited in claim 13, further comprising:
    a surgical instrument movably disposed in an operating channel.

17. A device as recited in claim 13, further comprising energy transmission elements disposed on said protective member.

18. A device as recited in claim 13, further comprising energy sensors disposed on said protective member.

19. A surgical ablation device comprising:
    means for transmitting ablation energy to or from anatomical tissue;
    an elongated body having a distal end adapted to insertion into an anatomical cavity and a proximal end adapted to manipulation from outside the anatomical cavity; and
    a cupping element disposed on said distal end and being sized and adapted to substantially envelope a surface of the anatomical tissue, the cupping element operative to move to and between a closed state and an opened state, wherein, in the closed state, the distal end of the elongated body is inserted into the anatomical cavity and, in the opened state, the cupping element in the anatomical cavity receives the anatomical tissue so that the cupping element can move towards the closed state to substantially envelope the anatomical tissue.

20. A device as recited in claim 19, wherein said elongated body comprises a tubular inner member disposed at least partly inside a tubular outer member, said outer member being slidable with respect to said inner member.

21. A device as recited in claim 20, wherein said protective cap comprises at least one protective member, each of said protective members comprising a cover disposed on at least one flexible arm extending from a distal end of said inner member.

22. A device as recited in claim 21, further comprising:
    means for causing relative sliding movement of said outer member with respect to said inner member, movement of said outer member distally over said inner member causing said flexible arms to move toward a central longitudinal axis of said device to permit said protective members to move between an open position, wherein said protective members extend beyond radial dimensions of said outer member, and a closed position wherein said protective members are contained essentially within the radial dimensions of said outer member.

23. A device as recited in claim 22, wherein said protective members are spoon shaped when in the open position.

24. A device as recited in claim 19, further comprising:
    at least one operating channel defined in said inner member.

25. A device as recited in claim 19, further comprising:
    a surgical instrument movably disposed in an operating channel.

26. A device as recited in claim 19, wherein said protective cap is a thermal insulator and the ablation energy is in the form of heat transmitted to the tissue.

27. A device as recited in claim 19, wherein said protective cap is a thermal insulator and the ablation energy is transmitted from the tissue to lower the temperature of the tissue.

28. A device as recited in claim 19, wherein said protective cap is an electromagnetic insulator and a thermal insulator and the ablation energy is electromagnetic radiation.

29. A device as recited in claim 19, wherein said means for transmitting comprises transmission elements disposed on said protective cap.

30. A protective device for internal anatomical tissue disposed within an anatomical cavity comprising:

at least one cupping element adapted to be disposed around the internal anatomical tissue, the cupping element operative to move to and between a closed state and an opened state, wherein, in the closed state, the cupping element can be inserted into the anatomical cavity and, in the opened state, the cupping element in the anatomical cavity receives the anatomical tissue so that the cupping element can move towards the closed state to substantially envelope the anatomical tissue.

* * * * *